United States Patent
Wu

(10) Patent No.: US 12,070,508 B2
(45) Date of Patent: Aug. 27, 2024

(54) MICROPARTICLES AND NANOPARTICLES HAVING SULFATE GROUPS ON THE SURFACE

(71) Applicant: CYTODIGM, INC., Natick, MA (US)

(72) Inventor: Bin Wu, Lexington, MA (US)

(73) Assignee: Cytodigm, Inc., Natick, MA (US)

( * ) Notice: Subject to any disclaimer, the term of this patent is extended or adjusted under 35 U.S.C. 154(b) by 0 days.

(21) Appl. No.: 17/534,146

(22) Filed: Nov. 23, 2021

(65) Prior Publication Data

US 2022/0175959 A1 Jun. 9, 2022

Related U.S. Application Data

(63) Continuation of application No. PCT/US2020/034842, filed on May 28, 2020.

(60) Provisional application No. 62/853,302, filed on May 28, 2019.

(51) Int. Cl.

| | | |
|---|---|---|
| A61K 31/737 | (2006.01) | |
| A61K 9/50 | (2006.01) | |
| A61K 9/51 | (2006.01) | |
| A61K 47/69 | (2017.01) | |
| B82Y 5/00 | (2011.01) | |

(52) U.S. Cl.
CPC ........ *A61K 47/6937* (2017.08); *A61K 9/5005* (2013.01); *A61K 47/6907* (2017.08); *B82Y 5/00* (2013.01)

(58) Field of Classification Search
None
See application file for complete search history.

(56) References Cited

U.S. PATENT DOCUMENTS

| | | |
|---|---|---|
| 6,486,232 B1 | 11/2002 | Wise et al. |
| 10,780,053 B2 | 9/2020 | Wu |
| 2008/0124400 A1 | 5/2008 | Liggins et al. |
| 2010/0322908 A1 | 12/2010 | Everland et al. |
| 2014/0256695 A1* | 9/2014 | Nguyen ............... A61L 27/26 514/180 |
| 2015/0196516 A1* | 7/2015 | Yacoub ............... A61K 9/5146 514/255.06 |
| 2016/0310426 A1 | 10/2016 | Wu |
| 2018/0206480 A1 | 7/2018 | Ghosh |
| 2019/0046448 A1 | 2/2019 | Wu |

FOREIGN PATENT DOCUMENTS

| | | |
|---|---|---|
| CN | 106038512 A | 10/2016 |
| WO | 2018111851 A1 | 6/2018 |
| WO | 2018111951 A1 | 6/2018 |

OTHER PUBLICATIONS

Fan J, Liu Y, Wang S, Liu Y, Li S, Long R, Zhang R, Kankala RK. Synthesis and characterization of innovative poly (lactide-co-glycolide)-(poly-L-ornithine/fucoidan) core-shell nanocarriers by layer-by-layer self-assembly. RSC advances. 2017;7(52):32786-94. (Year: 2017).*

Dang X, Gu L, Qi J, Correa S, Zhang G, Belcher AM, Hammond PT. Layer-by-layer assembled fluorescent probes in the second near-infrared window for systemic delivery and detection of ovarian cancer. Proceedings of the National Academy of Sciences. May 10, 2016;113(19):5179-84. (Year: 2016).*

Lu KY, Li R, Hsu CH, Lin CW, Chou SC, Tsai ML, Mi FL. Development of a new type of multifunctional fucoidan-based nanoparticles for anticancer drug delivery. Carbohydrate polymers. Jun. 1, 2017;165:410-20. (Year: 2017).*

Cunha, L., et al., "Sulfated Seaweed Polysaccharides as Multifunctional Materials in Drug Delivery Applications", Mar Drugs, 14(42) 2016; doi: 10.3390/md14030042.

Lamichhane, S. P., et al., "Glycosaminoglycan-functionalized poly-lactide-co-glycolide nanoparticles: synthesis, characterization, cytocompatibility, and cellular uptake", Int. J. Nanomedicine, 10: 775-789 (2015).

* cited by examiner

*Primary Examiner* — Nissa M Westerberg

(74) *Attorney, Agent, or Firm* — Elmore Patent Law Group, P.C.; Carolyn S. Elmore; Jia Kang

(57) ABSTRACT

This invention provides polymer particles which contain negative charges on the surface of the particle. Preferably, the particles comprise PLGA and sulfate polymer. The invention also provides polymer particle produced by the methods of the invention.

7 Claims, No Drawings

MICROPARTICLES AND NANOPARTICLES HAVING SULFATE GROUPS ON THE SURFACE

RELATED APPLICATIONS

This application is a continuation of International Application No. PCT/US20/34842, which designated the United States and was filed on May 28, 2020, published in English, which claims the benefit of U.S. Provisional Application No. 62/853,302, filed on May 28, 2019. The entire teachings of the above applications are incorporated herein by reference.

ABSTRACT

This invention provides a pharmaceutical composition comprising microparticles and nanoparticles comprising a pharmaceutically acceptable polymer and at least one sulfated agent. This invention also provides the method of preparing said pharmaceutical composition.

BACKGROUND OF THE INVENTION

Many therapeutic agents need to be delivered to certain targets in the human body. Such target can be an organ, a certain type of tissue, or a specific receptor on a cell. Due to the lack of targeting many drugs could not fully realize their optimal therapeutic potential and even cause adverse effects. For example, only a small fraction of chemotherapeutic agents administered systemically reached tumor sites. In the field of immunology and immuno-oncology, it is often desired that a drug molecule be delivered to a specific type of cell. One strategy for targeting cells is to use antibody to bind a receptor on the cell of interest. A drug molecule can be conjugated to an antibody which guides the drug to the cell followed by antibody binding the cell receptor and drug being internalized by the cell. A drug can also be encapsulated into a nanoparticle and an antibody is then conjugated to said drug-loaded nanoparticle. Thus, the antibody guides the nanoparticle to the cell of targeting.

There has been some success in using such antibody-nanoparticle strategy to deliver drugs to the targeted sites. However, this approach has disadvantages. For example, antibodies are prone to hydrolysis and degradation in the body fluid and as a result, a significant portion of the antibody administered may lose its activity due to the hydrolysis and degradation. In addition, developing and producing antibodies are costly.

We have proposed microparticles and nanoparticles with highly negative zeta potentials formed by incorporating polyanionic polymers, such as polyacrylic acid and hyaluronic acid, into PLGA particles and their use in treating a variety of diseases. See, WO2014/089160, which is incorporated herein by reference in its entirety.

There is a need to prepare negatively charged microparticles and nanoparticles with enhanced therapeutic properties.

SUMMARY OF THE INVENTION

One aspect of the invention provides microparticles and nanoparticles having a high negative surface charge, or zeta potential, and methods for the preparation thereof. The microparticles and/or nanoparticles preferably comprise poly(lactic-co-glycolic acid) (PLGA), a sulfated polymer, such as a sulfated polysaccharides and, optionally, an active agent. The sulfated polysaccharide is preferably added in an amount effective to impart a negative zeta potential having an absolute value of at least 25 mV, preferably at least about 30 mV and more preferably at least about 35 mV. The sulfated polymer is also referred to herein as "an anionic polymer" or "negatively charged agent."

The sulfated polymer may be synthetic or of natural origin. An originally non-sulfated polymer can be sulfated chemically to become a sulfated polymer. Depending on the degree of an agent being sulfated, the sulfated polymer can be slightly sulfated or highly sulfated. Highly sulfated polymer can provide more highly negative charges to the surface of said microparticles and nanoparticles. Examples of sulfated polysaccharides include heparan sulfate, carrageenan, fucoidan, and ulvan (Ludmylla Cunha and Ana Grenha, *Mar. Drugs* 2016, 14, 42; Medeiros, G. F. et al, *Biochimica et Biophysica Acta (BBA)—General Subjects*, 1475 (3): 287-294; Emiliano Bedini, et al, *Carbohydrate Polymers*, 174 (2017), 1224-1239; Dai-Hung Ngo and Se-Kwon Kim, *Inter. J. Bio. Macrom.*, 62 (2013), 70-75.) Preferably, the sulfate polymer is not heparin.

The invention includes a method for the preparation of microparticles or nanoparticles comprising: (1) dissolving PLGA (and optionally an active agent, such as a pharmaceutical ingredient (API), or a poorly water soluble compound) in a first solvent to form a PLGA solution; (2) emulsifying the polymer solution in a solution of a second solvent to form an emulsion, wherein the first solvent is not miscible or partially miscible with the second solvent, and wherein the solution of the second solvent comprises a sulfated polymer, said solution of the second solvent optionally further comprising a surfactant and/or an API soluble in the second solvent; and, (3) removing the first solvent to form said microparticles or nanoparticles having negative surface charges.

The invention also provides a method for the preparation of microparticles or nanoparticles having negative surface charges, said method comprising: (1) dissolving PLGA (and optionally an active agent, an API, or a poorly water soluble compound) in a first solvent to form a polymer solution; (2) adding a second solvent to the polymer solution to form a mixture, wherein the first solvent is not miscible or partially miscible with the second solvent, and wherein the first solution of the second solvent optionally comprises an active agent which may be the same or different; (3) emulsifying the mixture to form a first emulsion; (4) emulsifying the first emulsion in a second solution of the second solvent to form a second emulsion, wherein the second solution of the second solvent comprises a sulfated polymer, and optionally further comprises a surfactant; and, (5) removing the first solvent to form microparticles or nanoparticles having negative surface charges.

Preferably, the method further comprises washing said microparticles or nanoparticles, and/or concentrating said microparticles or nanoparticles to a desired volume.

Preferably, the negative surface charges can sustain certain washing tests, such as the wash test exemplified herein, without significantly losing the negative surface charges as measured by zeta potential (e.g., does not become significantly less negative—a negative value closer to 0 than the original negative value).

Preferably, after washing, the microparticles or nanoparticles retain at least about 75%, 80%, 85%, 90%, 95%, or 99% of the negative surface charges as measured by zeta potential.

Preferably, the PLGA has an average molecular weight of from about 500 to about 1,000,000 Da, preferably from about 1,000 to about 100,000 Da.

Preferably, the PLGA has an L/G ratio of from about 100/0 to 0/100, about 95/5 to 5/95, about 85/15 to 15/85, and about 50/50.

Preferably, the PLGA contains multiple negatively charged terminal groups, such as carboxyl groups.

Preferably, the microparticles or nanoparticles have a zeta potential of about −25 mV or lower, about −30 mV or lower, about −35 mV or lower, −40 mV or lower, about −45 mV or lower, or about −50 mV or lower. Such as −40 mV to −65 mV.

Preferably, the first solvent is methylene chloride, ethyl acetate, or chloroform.

Preferably, the solution of the second solvent is aqueous and preferably comprises a surfactant comprising organic or inorganic pharmaceutical excipients; various polymers; oligomers; natural products; nonionic, cationic, zwitterionic, or ionic surfactants; and mixtures thereof. Preferred surfactants include polyvinyl alcohol (PVA), polyvinylpyrrolidone (PVP), a Tween series surfactant, Brij series surfactant, Pluronic series, Poloxamer series, or Triton X-100 or a salt, derivative, copolymer, or mixture thereof.

Preferably, the emulsifying step comprises homogenization, mechanical stirring, and/or microfluidization.

Preferably, the first solvent is removed through solvent exchange and/or evaporation.

Preferably, the microparticles or nanoparticles comprise an active agent, such as an API (active pharmaceutical ingredient).

Preferably, the API is encapsulated within the microparticles or nanoparticles.

Alternatively or additionally, the API can be covalently or ionically attached to the surface of the microparticles or nanoparticles. For example, the API can be covalently attached to the particle surface via a hydrolysable bond (e.g., an ester or amide) that facilitates in vivo release.

Preferably, the solution of the second solvent further comprises, or is saturated with, the first solvent before the PLGA solution in the first solvent is added to the solution of the second solvent during emulsification. This may be beneficial in that the PLGA in the first solvent is less likely to precipitate when added to the solution of the second solvent for emulsification. Preferably, the first solvent is ethyl acetate, and the solution of the second solvent (e.g., water or aqueous solution) comprises about 7-8% v/v of ethyl acetate.

It should be understood that any preferred features of the invention described herein can be combined with any other preferred features, including preferred features described only under one aspect of the invention, and preferred features described only in the examples.

DETAILED DESCRIPTION OF THE INVENTION

1. Overview

In the field of pharmaceutical and biotechnology, it is often desirable to encapsulate a drug/API into polymeric particles. For example, a drug can be encapsulated into microparticles (also referred to herein as microspheres) of biodegradable polymers such as poly(lactide-co-glycolide), PLGA, for long-acting, sustained release. Examples of commercialized products include PLGA or PLA microspheres of leuprolide acetate, exenatide, risperidone, and naltrexone.

In addition to microsphere formulations, drug molecules can also be encapsulated into polymeric nanoparticles for targeted drug delivery, which involves delivering drugs to specific sites, cells, organs and receptors. For example, nanoparticles can deliver drugs into tumor tissues utilizing "Enhanced Permeability and Retention Effect" or EPR effect. EPR effect is the property by which molecules or particles of certain sizes tend to accumulate in tumor tissues much more so than they do in normal tissues (Matsumura and Maeda, Cancer Research. 46 (12 Pt 1): 6387-6392, 1986; Duncan and Sat, *Ann. Oncol.* 9, Suppl. 2: 39, 1998; Kaye, et al. Clinical Cancer Research. 5 (1): 83-94, 1999).

Targeted drug delivery may also be achieved by first encapsulating a drug into nanoparticles, followed by attaching a targeting agent on the surface of the nanoparticles. In most cases, it is required that the attachment of the targeting agent to the surface be done via a chemical conjugation. Typically, such conjugation involves chemical reactions between the targeting agent and appropriate reactive groups on the surface of the nanoparticles. Reactive groups include carboxyl, amino, thiol, aldehyde, maleimide, epoxide, and anhydride.

Polylactide (PLA), PLGA, polycaprolactone (PCL) and several other biodegradable and biocompatible polymers have been used to encapsulate APIs for a large variety of applications.

The surface properties of such polymeric particles can be very important for targeted drug delivery. There are at least the following two aspects relating to the surface properties of drug loaded particles that can be considered:
1) The surface charge—for each specific drug delivery application, the particle surface may need to be positive, negative or neutral; and the zeta potential may need to be in a specific range.
2) Functional groups on the surface—for conjugation with a biological entity or targeting agent on the surface of drug loaded particles; examples include carboxyl, amino, thiol, aldehyde, maleimide, glycidyl, and anhydride to the surface.

In some cases, one can achieve both goals with a single solution. For example, sulfate groups can be added to the surface of drug loaded polymeric particles to generate negative charges and functional groups on the surface at the same time.

The invention described herein provides pharmaceutical formulations comprising microparticles and nanoparticles (with or without agent/drug/API load), as well as improved processes capable of producing such pharmaceutical formulations comprising microparticles and nanoparticles, with high surface density of sulfate groups, and highly negative surface charges, using only pharmaceutically acceptable ingredients.

The invention is partly based on the discovery that microparticles and nanoparticles manufactured in the process of the present invention from the coprecipitation or coacervation of a hydrophobic and/or neutral biocompatible polymer, such as PLGA or PLA, and a sulfate polymer provide a high density of anions on the surface of the particles, which can improve the immunogenic properties with the ability to encapsulate an active agent in high loads. Without being bound by any theory, it is believed that the polymer backbones intertwine or interlace while in the organic phase of emulsion, while the hydrophilic anions favor the surface of the emulsion droplet. The interconnecting network thus formed results in a particle where the otherwise water soluble anionic polymer cannot be washed away and simultaneously preserves a hydrophobic microenvironment beneficial to encapsulation.

As used herein, "small (amount)," in the context of the amount of solvent, refers to a relatively small amount/ volume of the first solution of the second solvent as compared to the volume of the first solvent with PLGA polymer, such that emulsification of the first solution of the second solvent in the polymer solution in the first solvent forms an emulsion (i.e., the first emulsion) with the continuous phase being the polymer solution. Typically, the volume ratio between the small amount of the first solution of the second solvent, and the first solvent, is at least about 1:n, wherein n can be 1, 2, 3, 4, 5, 6, 7, 8, 9, 10, 20, 30, 40, 50, 60, 70, 80, 90, or 100.

As used herein, "large (amount)" refers to the relatively large amount/volume of the second solution of the second solvent as compared to the volume of the first emulsion, such that emulsification of the first emulsion in the second solution of the second solvent forms an emulsion (i.e., the second emulsion) with the continuous phase being the second solution of the second solvent. Typically, the volume ratio between the first emulsion and the large amount of the second solution of the second solvent, is at least about 1:m, wherein m can be 1, 2, 3, 4, 5, 6, 7, 8, 9, 10, 20, 30, 40, 50, 60, 70, 80, 90, or 100.

Preferably, large scale production results in microparticles or nanoparticles having a zeta potential of about −40 mV or lower, about −45 mV or lower, or about −50 mV or lower. An alternative way to state the property is that the zeta potential is negative and the absolute value of the zeta potential is greater than 40 mV, or greater than 45 mV or greater than 50 mV.

Using the methods of the invention, the sulfate polymer is tightly integrated into the produced microparticles or nanoparticles. Thus, preferably, the sulfate polymer is incorporated onto said microparticles or nanoparticles and increases negative surface charges on said microparticles or nanoparticles.

The incorporation of the pharmaceutically acceptable negatively charged agent into the microparticles or nanoparticles can be stable and tight. Thus, preferably, the method further comprises washing said microparticles or nanoparticles, and/or concentrating said microparticles or nanoparticles to a desired volume.

While not wishing to be bound by any particular theory, the negative surface charges due to the presence of the sulfate groups, are tightly anchored on the surface of the microparticles and nanoparticles, and can thus sustain various washing conditions or washing tests without suffering from significant loss of such negative surface charges and/or sulfate groups.

The microparticles and nanoparticles produced using the methods of the invention may routinely undergo washing as part of a purification process that removes impurity, and/or concentrates the microparticles and nanoparticles so produced.

The microparticles and nanoparticles produced using the methods of the invention may also undergo more stringent washing tests, e.g., as part of the quality control process, to ensure that the negative surface charges and/or carboxyl groups are stably incorporated into the microparticles and nanoparticles so produced.

Preferably, the washing test uses conditions identical to or similar to those exemplified below. Preferably, after the washing test, the microparticles and nanoparticles do not significantly lose the negative surface charges as measured by zeta potential (e.g., does not become significantly less negative—a negative value materially closer to 0 than the original negative value or having a lower absolute value).

Preferably, the microparticles or nanoparticles retain at least about 75%, 80%, 85%, 90%, 95%, or 99% of the negative surface charges as measured by zeta potential after washing.

With the invention generally described above, specific aspects of the invention are described further in the sections below.

2. Definitions

As used herein, "pharmaceutically acceptable" includes those compounds, materials, compositions, and/or dosage forms which are, within the scope of sound medical judgment, suitable for medical or veterinary use when in contact with the tissues of human beings and animals at the concentration, dosage or amount present in the product, without causing excessive toxicity, irritation, allergic response, or other problems or complications, commensurate with a reasonable benefit/risk ratio. Preferably, a pharmaceutically acceptable material (e.g., polymer, excipient, surfactant, solvent or microparticles/nanoparticles produced therefrom) is suitable or approved for human medical use.

As used herein, "microparticles" are preferably roughly round, sphere, or sphere-like in shape, and are generally within the size range of, e.g., between about 1-1,000 µm, or between about 10-100 µm, as measured by laser diffraction, for example. The subject microparticles may also include particles that are less likely to clump or aggregate in vivo. However, it is understood that other particle morphologies are possible as well, including rods, plates, sheets, and needles. Typically, it is understood that the particle size reflects the volume median geometric size of the product sample tested.

As used herein, "nanoparticles" are preferably roughly round, sphere, or sphere-like in shape, and are generally within the size range of, e.g., between about 1-1,000 nm, between about 10-1,000 nm, or between about 50-1,000 nm, or between about 100-500 nm, as measured by laser diffraction or dynamic light scattering, for example. The subject nanoparticles may also include particles that are less likely to clump in vivo.

Particle size and size distribution can be measured by a dynamic light scattering instrument, e.g., a Malvern Zetasizer. Alternative techniques include, for example, sedimentation field flow fractionation, photon correlation spectroscopy, light scattering, dynamic light scattering, light diffraction, and disk centrifugation. The terms "microparticle" and "nanoparticle" are not intended to convey any specific shape limitation. Such particles, include, but are not limited to those having a generally polyhedral or spherical geometry. Preferred particles are characterized by a spherical geometry typically produced by emulsion-based encapsulation processes. It is understood that the terms "microparticle" and "nanoparticle" are often used interchangeably herein, unless accompanied by a specific description of size. For example, the term "microparticles" is intended to also embrace "nanoparticles" as if stated as "microparticles and/or nanoparticles" unless the context demands otherwise.

It is not necessary that each microparticle or nanoparticle be uniform in size, although they can be generally of a size sufficient to trigger phagocytosis in an antigen presenting cell (APC) or other mononuclear phagocyte system (VIPS) cell. Preferably, the subject microparticles and nanoparticles have a diameter sufficient to trigger phagocytosis in an antigen presenting cell (APC) or other MPS cell.

In accordance with the invention, the microparticles or nanoparticles have a negative (surface) charge. The negative charge density on the sulfated microparticles and nanoparticles can be quantified by "zeta potential." The zeta potential of the microparticles and nanoparticles having a negative surface charge is typically measured in an aqueous suspension of the particles at a pH of from 4 to 10, preferably from 5 to 8. Preferably, the microparticles or nanoparticles produced by the methods of the invention may have a zeta potential of from about −20 mV to about −200 mV, preferably from about −30 mV to about −100 mV, most preferably from −35 mV to −85 mV. A zeta potential more negative than about −40 mV are referred to herein as "highly negatively charged particles".

As used herein, "about" generally means up to ±10% of the particular term being modified.

The term, "sulfate polymer," is used herein to define polymers comprising one or more monomers having a pendant sulfate moiety. Sulfate polymers may be synthetic or of natural origin. An originally non-sulfated polymer can be sulfated chemically to become a sulfated polymer. Depending on the degree of an agent being sulfated, the sulfate polymer can be slightly sulfated or highly sulfated. Highly sulfated polymer can provide more highly negative charges to the surface of said microparticles and nanoparticles. Preferably, the polymer backbone is a polysaccharide and the sulfate polymer is a sulfate polysaccharide.

3. PLGA

PLGA is typically prepared by ring-opening polymerization of lactide and glycolide. In this reaction, Stannous octoate is usually used as the catalyst, although other catalysts may also be used. An initiator, such as an alcohol, is often used to initiate the polymerization reaction. If no initiator is intentionally added, trace amount of polar compound containing an active proton, such as alcohol and water, may serve as the initiator. Polymerization usually results in a PLGA polymer with a carboxyl group at the chain terminal, as illustrated below:

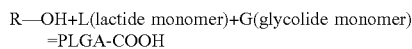
R—OH+L(lactide monomer)+G(glycolide monomer)
=PLGA-COOH

Therefore, each PLGA and/or PLA polymer molecule is typically linear, and typically contains a single COOH group at the chain terminal. Consequently, conventional PLGA/PLA particles prepared from such PLGA/PLA polymers have small amount of COOH groups on the surface, and the negative charge thereon may not be sufficient for certain uses, such as cell targeting and the treatment of disease, such as cancer or inflammatory diseases. In addition, there may not be sufficient numbers of COOH groups for covalently attaching API's or other chemical moiety such as protein ligands or other targeting agents to the surface of said microparticles and nanoparticles. Such protein ligands or other targeting agents may bind to a receptor or a binding partner on the surface of a target cell, tissue, organ, or location.

The instant invention provides various methods or combinations thereof for producing PLGA/PLA particles with additional negatively charged groups (e.g., carboxyl groups) on the PLGA/PLA particle surfaces. Such PLGA/PLA particles with increased net negative surface charges are particularly useful, for example, to target certain cells to cause immune reactions, treat disease, such as cancer or inflammatory diseases and to facilitate the conjugation of API's or other chemical entity to the microparticles and nanoparticles.

Preferably, the average molecular weight of the pharmaceutically acceptable polymer PLGA is within a desired range.

The low end of the range is preferably no less than about 100, 200, 300, 400, 500, 600, 700, 800, 900, 1000, 1200, 1500, 2000, 2500, or 3000 Da. The desired range has a low end of any of the above values.

The high end of the range is preferably no more than 500,000, 400,000, 300,000, 200,000, 100,000, 75,000, 50,000, 40,000, 35,000, 30,000, 25,000, 20,000, 15,000, 10,000, 7,500, or 5,000 Da. The desired range has a high end of any of the above values.

For instance, the desired range may be from about 500 to about 200,000 Da, or from about 1,000 to about 100,000 Da.

Preferably, the PLGA has an average molecular weight of from about 500 to about 1,000,000 Da, preferably from about 1,000 to about 100,000 Da.

For PLGA, average molecular weight can be expressed in other physical properties such as inherent viscosity. Inherent Viscosity (IV) is a viscometric method for measuring molecular size. IV is based on the flow time of a polymer solution through a narrow capillary relative to the flow time of the pure solvent through the capillary. For certainty measures in the instant application, the solvent used is typically chloroform, and the polymer concentration is about 0.5% (w/v). The temperature at which the viscosity is measured is about 30° C. The units of IV are typically reported in deciliters per gram (dL/g). Thus, for example, PLGA used in the instant invention may have an inherent viscosity of from about 0.01 to about 20 dL/g, or from about 0.05 to about 2.0 dL/g.

The composition and biodegradability of the subject PLGA polymer is partly determined by the molar ratio of lactide (L) to glycolide (G) unit in the polymer, or L/G ratio. The L/G ratio of the PLGA polymer in the present invention can be from 100/0 to 0/100. As used herein, an L/G ratio of "100/0" refers to polylactide or PLA, and an L/G ratio of "0/100" refers to polyglycolide, or PGA. Preferably the L/G ratio for the PLGA polymer is from about 100/0 to 0/100, or about 95/5 to 5/95, more preferably from about 85/15 to 15/85. The most preferable L/G ratio in the present invention is about 50/50.

Other polymers can be mixed with the PLGA polymer in the preparation of the PLGA microparticles and nanoparticles. For example, polyethylene glycol, or PEG, is often added to the PLGA for enhanced performance. PEGylated particles are useful because they often have increased circulation time in human or animal bodies.

Preferably, copolymers of PEG and PLGA can also be used.

The microparticles and nanoparticles prepared from the PEG and PLGA mixture or PEG and PLGA copolymer are referred to as PEGylated PLGA microparticles and nanoparticles.

Such "PEGylation" process can also be done after microparticles and nanoparticles are formed. In this case, PEG polymers or other polymers containing PEG units are coated via physical absorption onto the PLGA microparticles and nanoparticles.

The PEG units can also be attached to the surface of PLGA microparticles or nanoparticles via covalent bonds. Such process is often referred to as "conjugation." In a conjugation process, a reactive entity containing PEG units react with certain functional groups on the surface of the microparticles and nanoparticles to form chemical bonds.

Thus, preferably, the pharmaceutically acceptable polymer is PLGA, and the microparticles or nanoparticles are PEGylated. The microparticles or nanoparticles may be PEGylated by mixing polyethylene glycol (PEG) or PEG-containing entity during the preparation of the microparticles and nanoparticles. The microparticles or nanoparticles may also be PEGylated by using copolymers of PEG and PLGA. The microparticles or nanoparticles can further be PEGylated by physically absorbing PEG polymers or polymers containing PEG units onto the PLGA microparticles and nanoparticles. The microparticles or nanoparticles may additionally be PEGylated by conjugating PEG units to the surface of the PLGA microparticles or nanoparticles via covalent bonds.

4. Sulfate Polymers

Sulfate polymers may be synthetic or of natural origin. An originally non-sulfated polymer can be sulfated chemically to become a sulfated polymer. Depending on the degree of an agent being sulfated, the sulfate polymer can be slightly sulfated or highly sulfated. Highly sulfated polymer can provide more highly negative charges to the surface of said microparticles and nanoparticles. Preferably, the polymer backbone is a polysaccharide and the sulfate polymer is a sulfate polysaccharide.

Examples of sulfated polysaccharides, such as sulfated glycosamineglycans (GAGs) include heparan sulfate, carrageenan, fucoidan, ulvan and sulfated colominic acid (Ludmylla Cunha and Ana Grenha, *Mar. Drugs* 2016, 14, 42; Medeiros, G. F. et al, *Biochimica et Biophysica Acta (BBA)—General Subjects,* 1475 (3): 287-294; Emiliano Bedini, et al, *Carbohydrate Polymers,* 174 (2017), 1224-1239; Dai-Hung Ngo and Se-Kwon Kim, *Inter. J. Bio. Macrom.,* 62 (2013), 70-75.)

Preferred heparan sulfates include linear polysaccharides comprising an amino sugar (such as N-acetyl-D-glucosamine and/or N-acetyl-D-galactosamine) and a uronic acid (such as D-glucoruronic acid or L-iduronic acid) and typically have the schematic structure: →4GlcAβ1→4GlcNAcα1→. Heparan sulfates can be synthetically produced or isolated from natural tissues. Heparan sulfates can preferably be 5-70 or more kDa; have between about 0.8 to 1.8 or more sulfates per hexosamine. Low molecular weight heparan sulfates are preferred, e.g., less than about 15 kDa. The ratio of the amino sugar(s) and uronic acid(s) is not critical and can range from 0 to 100%, preferably 25 to 75%, such as between 30 and 70%.

Naturally occurring ulvan (rhamnan sulfate) can be isolated from green seaweed. However, synthetically produced ulvans can be used as well. Ulvan is commonly characterized by uronic acid and rhamnose sulfate, can have a schematic structure: →4βGlcA1→4αL-Rhaα 3S1→4αL-IdoA1→Rhaα 3S1→. The ulvan can have a molecular weight between 1 and 2000 kDa, such as 10-100 kDa. Low molecular weight ulvan are preferred, e.g., less than about 15 kDa. The degree of sulfation (the percentage of rhamnose that has been sulfated) can be between 1 and 75%, such as between 1 and 40%.

Carrageenan is a sulfated polygalactan commonly characterized by D-galactose and 3,6-anhydro-galactose joined by an alpha-1,3 and beta-1,4 linkage. Typically the carrageenan can have between 10-50% or more sulphate groups, such as between about 22-35% sulfates. The molecular weights can be between 5 kDa and 800 kDa, such as between 20 and 30 kDa (degraded carrageenans) or 200 to 400 kDa. Low molecular weight carrageenans are preferred, e.g., less than about 15 kDa.

Fucoidan is typically characterized by sulfated esters of fucose and glucuronic acid and can have a molecular weight between about 5 and 30 kDa or more. The degree of sulfation (percentage of fucose sugars that have been sulfated) can be at least about 25%, such as at least about 50% or at least about 90% or more. Low molecular weight fucoidans are preferred, e.g., less than about 15 kDa.

Polysaccharides refers to polymers made of a plurality of sugars. The sugars can be natural (e.g., glucose, fructose, galactose, mannose, arabinose, ribose, deoxyribose, xylose, erythrose, allose, altrose, gulose, sorbose, tagatose, lyxose, ribulose, erythrulose, threose, fucose and rhamnose). The sugars can also be modified, such as aminated sugars (e.g., galactosamine, glucosamine or sialic acid), acetylated amino sugars, fluorinated sugars, deoxy sugars (e.g., fucose or rhamnose) and the like. The sugar monomer can be sulfated prior to making the polysaccharide and/or the polysaccharide can be sulfated. It is believed that the polysaccharides of the invention will have improved clearance properties and metabolism.

Sulfated alcohol or amine polymers can also be desirable. An example of a sulfated alcohol polymer includes sulfated polyvinyl alcohol (PVAS) or a sulfated copolymer of vinyl alcohol and acrylic acid (PAVAS). The degree of sulfation can be at least about 10% (percentage of sulfated vinyl alcohol), such as at least about 40% or at least about 70%.

The negative surface charge can be measured using any technique known in the art, such as by measuring zeta potential (see Examples).

Preferred polymers having a molecular weight of at least 1,000 (1K) g/mol, preferably at least 3K, at least 5K, at least 10K, at least 15K, at least 20K, at least 25K, at least 30K, at least 35K, at least 40K, at least 45K, at least 50K, at least 75K, at least 100K, at least 150K, at least 200K, at least 250K, at least 300K, at least 350K, at least 400K, at least 450K, at least 500K, at least 550K or at least 600K or more. Optimizing the polymer chain can facilitate the formation of a durable interpenetrating network. Where the polymer is too small, the polymer's surfactant properties may interfere with network formation. However, a chain that is too long or excessively highly branched can prevent good entanglement. Low molecular weight sulfate polysaccharides are preferred, e.g., between about 200 Da and 15 kDa, preferably between about 5 kDa and 15 kDa.

In addition, the polymer can be substituted covalently or ionically along the length of the chain or at the termini of the chain. For example, one or more polysaccharides can be substituted by a targeting moiety, such as a cell ligand (or fragment), peptide, or sialic acid. The substitution or conjugation step of the targeting moiety can occur before the microparticle is formed or after.

The amount of the sulfate polymer used in the current invention can be from 0.01% to 30%, preferably from 0.1% to 15%, based on the weight of the pharmaceutically acceptable polymer (such as PLGA) used in the formulation.

5. Production of Nanoparticles or Microparticles with Enhanced Negative Surface

The invention described herein provides several basic methods for the preparation of particles with highly negative surface charges. These methods are not mutually exclusive and may be combined with one another to produce additive or even synergistic effects to produce microparticles and nanoparticles with highly negatively charged surfaces.

Thus in one aspect, the invention provides a method for the preparation of a composition comprising microparticles or nanoparticles having negative surface charges, the method comprising producing the microparticles or nanoparticles with a pharmaceutically acceptable polymer (e.g., PLGA) using either an emulsion process or a precipitation process (preferably the emulsion process, including the double emulsion process), wherein the method comprises any one or more features described below, or combination thereof.

Specifically, one feature of the methods of the invention comprises carrying out the emulsion process or the precipitation process in an aqueous solution having a pH that promotes ionization of the anionic polymer. While not wishing to be bound by any particular theory, the ionized groups or moieties, compared to their non-ionized forms, tend to be more exposed on the surface of the eventually formed microparticles or nanoparticles prepared using the methods of the invention.

An emulsion process may be used in the methods of the invention. Preferably, the subject microparticles and nanoparticles (e.g., PLGA microparticles and nanoparticles) can be prepared by an emulsification process comprising the following steps (not necessarily in this order): 1) dissolving the pharmaceutically acceptable polymer (e.g., PLGA) in a first solvent (e.g., methylene chloride) to form a polymer solution; 2) emulsifying the polymer solution (e.g., PLGA solution) in a solution of a second solvent (e.g., an aqueous solution, or an organic solvent) to form an emulsion, wherein the first solvent is not miscible or partially miscible with the second solvent, and wherein the solution of the second solvent optionally comprises anionic polymer (e.g., fucoidan, ulvan or heparan sulfate); and, 3) removing the first solvent to form the microparticles or nanoparticles having negative surface charges.

Preferably, at least one API is present in the nanoparticle or microparticle, and the emulsion process comprises: (1) dissolving said at least one API and the pharmaceutically acceptable polymer (e.g., PLGA) in a first solvent (e.g., an organic solvent) to form a polymer-API solution; (2) dissolving an anionic polymer (e.g., fucoidan, ulvan or heparan sulfate), in a second solvent (e.g., an aqueous solution) optionally comprising surfactants or surface stabilizing agents dissolved therein; (3) emulsifying the polymer-API solution in said second solvent/aqueous solution; and, (4) removing the first/organic solvent, such as by a solvent evaporation process or a solvent exchange process.

Preferably, in the emulsification process, the weight ratio of the PLGA solution to the aqueous solution is typically from 1:1,000 to 10:1, preferable from 1:100 to 1:1.

As used herein, miscibility is defined to be the property of liquids to mix in all proportions, forming a homogeneous solution. Substances/liquids are said to be immiscible or not miscible, if in some proportion, they do not form a solution.

Exemplary solvents miscible with water include acetone, tetrahydrofuran (THF), acetonitrile, dimethyl sulfoxide (DMSO), dimethylformamide (DMF).

A double emulsion process can be used, which may be particularly useful when an active pharmaceutical ingredient (API), such as a protein-based therapeutic prepared in an aqueous solution, is first emulsified with a pharmaceutically acceptable polymer solution to form a first emulsion such that the API is encapsulated within the polymer solution. Then the polymer, and the therapeutics encapsulated therein, is again emulsified in a larger volume of solvent to form a second emulsion (e.g., the water-in-oil-in-water or w/o/w type double emulsion), before the microparticle or nanoparticle is formed.

For example, in the above described w/o/w technique, a relatively small amount of a first solution of the second solvent (e.g., an aqueous protein solution) (e.g., about 20%, 15%, 10%, 5% v/v of the organic solvent) may be introduced into a relatively larger amount of a first solvent (e.g., an organic solvent), such as methylene chloride or ethyl acetate, that dissolves the hydrophobic polymer PLGA. The first emulsion is then formed using a suitable method, e.g., probe sonication or homogenization. After formation of the first emulsion, a second emulsion is formed by introducing the first emulsion into a larger volume of a second solution of the second solvent (e.g., about at least about 2-fold, 3-fold, 4-fold, 5-fold, 6-fold, 10-fold of the first emulsion) containing an emulsifier, e.g., polyvinyl alcohol. Again, a homogenization method can be used to form the second emulsion. This is next followed by a period of solvent evaporation leading to the hardening of the polymer, typically by stirring for some hours. As a result, the protein solution is trapped into the relative hydrophobic matrix of the PLGA polymer forming small inclusions. Finally, the microparticles or nanoparticles formed are collected, washed (e.g., with distilled water) via repeated centrifugation or filtration, followed by dehydration, typically by lyophilization.

Thus preferably, the subject microparticles and nanoparticles (e.g., PLGA microparticles and nanoparticles) can be prepared by a double emulsification process comprising the following steps (not necessarily in this order): 1) dissolving the pharmaceutically acceptable polymer (e.g., PLGA) in a first solvent (e.g., an organic solvent such as methylene chloride) to form a polymer solution; 2) adding a relatively small amount (e.g., less than about 20%, 15%, 10%, 5% v/v compared to that of the organic solvent) of a first solution of a second solvent into the polymer solution to form a mixture, wherein the first solvent is not miscible or partially miscible with the second solvent, and wherein the first solution of the second solvent optionally comprises an active pharmaceutical ingredient (API); 3) emulsifying the mixture to form a first emulsion; 4) emulsifying the first emulsion in a larger volume (e.g., at least about 2-fold, 3-fold, 4-fold, 5-fold, 6-fold, 10-fold of that of the first emulsion) of a second solution of the second solvent to form a second emulsion, wherein the solution of the second solvent optionally comprises the anionic polymer, and optionally further comprises a surfactant; and, 5) removing the first solvent to form said microparticles or nanoparticles having negative surface charges.

Preferably, at least one API is present in the nanoparticle or microparticle, and the emulsion process comprises: (1) dissolving a pharmaceutically acceptable polymer (e.g., PLGA) and optionally an API in a first solvent (e.g., an organic solvent) to form Solution A; (2) dissolving said API in a first solution of a second solvent (e.g., a $1^{st}$ aqueous solution) to form Solution B; (3) dissolving the anionic polymer, in a second solution of the second solvent (e.g., a $2^{nd}$ aqueous solution) to form Solution C, said $2^{nd}$ aqueous solution optionally comprises surfactants or surface stabilizing agents dissolved therein; (4) emulsifying Solution B in Solution A to form the first emulsion; (5) further emulsifying the first emulsion in Solution C to form the $2^{nd}$ emulsion; and, (6) removing the organic solvent of the $2^{nd}$ emulsion, such as by a solvent evaporation process or a solvent exchange process.

Preferably, the volume of the small amount of the solution of the second solvent added to the polymer solution for the generation of the first emulsion is typically from 0.01% to 50%, preferable from 0.1% to 10%, based on the volume of the PLGA solution.

Preferably, the volume ratio of the first emulsion to the $2^{nd}$ solution of the second solvent described as in Step 4) above is typically from 10:1 to 1:10,000, preferably from 1:1 to 1:100, such as 1:10 or 1:4-5.

A precipitation process may be used in the methods of the invention. Preferably, the subject microparticles and nanoparticles (e.g., PLGA microparticles and nanoparticles) can be prepared by a precipitation process comprising the following steps (not necessarily in this order): 1) dissolving the pharmaceutically acceptable polymer (e.g., PLGA) in a first solvent (e.g., acetone) to form a polymer solution; 2) preparing a solution of a second solvent (e.g., aqueous solution, such as 1 mM NaOH solution), wherein the first solvent is miscible with the second solvent, and wherein the solution of the second solvent optionally comprises the anionic polymer and optionally comprises a surfactant; and, 3) adding the polymer solution to the solution of the second solvent while mixing, thus forming the microparticles or nanoparticles having negative surface charges; wherein the solution of the second solvent is optionally the aqueous solution.

Preferably, the precipitation process comprises: (1) dissolving a pharmaceutically acceptable polymer (e.g., PLGA) and at least one API in a first solvent (e.g., an organic solvent) to form a polymer-API solution, said organic solvent is miscible with water; (2) dissolving an anionic polymer in a second solvent (e.g., an aqueous solution), said second solvent/aqueous solution optionally comprises surfactants or surface stabilizing agents dissolved therein; and, (3) combining (e.g. adding) the polymer-API solution to the aqueous solution while mixing, thus forming an API-loaded nanoparticles or microparticles having negative charges and carboxyl groups on the surface.

Preferably, in the precipitation process, the volume ratio of the PLGA solution to the aqueous solution is typically from 10:1 to 1:1,000, preferably from 1:1 to 1:10.

Preferably, as an alternative procedure to Step 3) in the precipitation process, the solution of the second solvent (e.g., the aqueous solution) can be added to the polymer solution (e.g., PLGA solution).

In any of the aspects involving an emulsion process described above, preferably, the first solvent is methylene chloride, ethyl acetate, or chloroform. Preferably, the $2^{nd}$ solution of the second solvent comprises a surfactant comprising organic or inorganic pharmaceutical excipients; various polymers; oligomers; natural products; nonionic, cationic, zwitterionic, or ionic surfactants; and mixtures thereof. The surfactant may comprise polyvinyl alcohol (PVA), polyvinylpyrrolidone (PVP), a polysorbate (Tween series) surfactant, a PEO-PPO-PEO polyethyleneoxide polypropylene oxide triblock copolymer (Pluronic series or Poloxamer series) surfactant, or a t-octylphenyl-polyethylene glycol (Triton X-100) surfactant or a salt, derivative, copolymer, or mixture thereof. Preferably, the surfactant is PVA (see examples).

Preferably, the emulsifying step comprises homogenization, mechanical stirring, and/or microfluidization.

Preferably, the first solvent is removed through solvent exchange and/or evaporation.

Preferably, the microparticles or nanoparticles have a negative (surface) charge. The negative charge density on the sulfated microparticles and nanoparticles can be quantified by zeta potential. The zeta potential of the sulfated microparticles and nanoparticles is typically measured in an aqueous suspension of the particles at a pH of from 4 to 10, preferably from 5 to 8. A Malvern particle size analyzer, such as the Nanosizer, (Worcestershire, UK) can measure the zeta potential according to factory instructions. Preferably, the microparticles or nanoparticles produced by the methods of the invention may have a zeta potential of from about −5 mV to about −200 mV, preferably from about −15 mV to about −100 mV, most preferably from −35 mV to −85 mV.

Preferably, the microparticles or nanoparticles have a zeta potential of about −40 mV or lower, about −45 mV or lower, or about −50 mV or lower, such as −40 mV to −65 mV.

6. Solvents and Surfactants

The solvent used in the dissolving step for the polymer can be any type of solvent that dissolves the polymer (e.g., PLGA). However, a volatile solvent is preferably used for its removal. For example, preferred solvents for forming the PLGA solution include methylene chloride, ethyl acetate, and chloroform.

In the emulsifying step, the (aqueous) solution may contain a surfactant or surface stabilizer. Surfactants generally include compounds that lower the surface tension of a liquid, the interfacial tension between two liquids, or that between a liquid and a solid. Surfactants may act as detergents, wetting agents, emulsifiers, foaming agents, and dispersants. Surfactants are usually organic compounds that are amphiphilic, which contain both hydrophobic groups (usually branched, linear, or aromatic hydrocarbon chain(s), fluorocarbon chain(s), or siloxane chain(s) as "tail(s)") and hydrophilic groups (usually heads). Surfactants are most commonly classified according to their polar head group: a non-ionic surfactant has no charge groups in its head; an ionic surfactant carries a net charge—if the charge is negative, the surfactant is anionic, and if the charge is positive, it is cationic. If a surfactant contains a head with two oppositely charged groups, it is termed zwitterionic. Preferably, anionic or zwitterionic surfactants, such as those containing carboxyl groups ("carboxylates"), are preferably used in the instant invention. The carboxylates are the most common surfactants and comprise the alkyl carboxylates, such as sodium stearate, sodium lauroyl sarcosinate, and carboxylate-based fluorosurfactants such as perfluorononanoate, perfluorooctanoate (PFOA or PFO).

While not wishing to be bound by any particular theory, surfactant may be useful for the formation and stabilization of the emulsion droplets. The surfactant may also comprise organic or inorganic pharmaceutical excipients, various polymers, oligomers, natural products, nonionic, cationic, zwitterionic, or ionic surfactants, and mixtures thereof.

The surfactants that can be used for the preparation of the subject (PLGA) microparticles/nanoparticles include polyvinyl alcohol, polyvinylpyrrolidone, Tween series, Pluronic series, Poloxamer series, Triton X-100, Brij series etc. Additional suitable surfactants are provided herein below.

The emulsification process may be carried out by any art-recognized means, such as homogenization, ultrasonication, mechanical stirring, microfluidization, or a combination thereof.

The removal of solvent is usually achieved by, for example, solvent exchange and evaporation.

Preferably, in order to ensure that most anionic groups are present on the surface of the subject (e.g., PLGA) microparticles and nanoparticles, the aqueous solution is adjusted to a pH that promotes ionization of a moiety on the polymers, such as a basic pH for a carboxyl group on PLGA and/or sulfate on the sulfate polymer. The pH is preferably in the range of about 4-14, 6-14, 6-10, or about 8-12, depending on the pKa of the polymer group that can become ionized to carry a negative charge. The pH of the aqueous solution can be adjusted to the preferred range by adding, for example, a base or a solution thereof, such as sodium hydroxide, potassium hydroxide, sodium bicarbonate, sodium carbonate, potassium bicarbonate, potassium carbonate, etc.

Combinations of more than one surfactant can be used in the invention. Useful surfactants or surface stabilizers which can be employed in the invention may include, but are not limited to, known organic and inorganic pharmaceutical excipients. Such excipients include various polymers, low molecular weight oligomers, natural products, and surfactants. Surfactants or surface stabilizers include nonionic, cationic, zwitterionic, and ionic surfactants.

Representative examples of other useful surfactants or surface stabilizers include hydroxypropyl methylcellulose, hydroxypropylcellulose, polyvinylpyrrolidone, sodium lauryl sulfate, sodium dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available TWEENS® such as e.g., TWEEN 20® and TWEEN 80® (ICI Specialty Chemicals)); polyethylene glycols (e.g., CARBOWAXS 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hydroxypropylmethylcellulose phthalate, noncrystalline cellulose, magnesium aluminum silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., PLURONICS F68® and F108®, which are block copolymers of ethylene oxide and propylene oxide); poloxamines (e.g., TETRONIC 908®, also known as POLOXAMINE 908®, which is a tetrafunctional block copolymer derived from sequential addition of propylene oxide and ethylene oxide to ethylenediamine (BASF Wyandotte Corporation, Parsippany, N.J.)); TETRONIC 1508® (T-1508) (BASF Wyandotte Corporation), TRITONS X-200®, which is an alkyl aryl polyether sulfonate (Rohm and Haas); CRODESTAS F-110®, which is a mixture of sucrose stearate and sucrose distearate (Croda Inc.); p-isononylphenoxypoly-(glycidol), also known as OLIN-1OG® or SURFACTANT 10-G® (Olin Chemicals, Stamford, Conn.); Crodestas SL-40 (Croda, Inc.); and SA9OHCO, which is C18H37CH2 (CON(CH3)-CH2(CHOH)4(CH2OH)2 (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-p-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-derivatized phospholipid, PEG-derivatized cholesterol, PEG-derivatized cholesterol derivative, PEG-derivatized vitamin A, PEG-derivatized vitamin E, lysozyme, random copolymers of vinyl pyrrolidone and vinyl acetate, polyethylene glycol alkyl ethers (Brij series surfactants) and the like.

Examples of useful cationic surfactants or surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), polyvinylpyrrolidone-2-dimethylaminoethyl methacrylate dimethyl sulfate, 1,2 Dipalmitoyl-sn-Glycero-3-Phosphoethanolamine-N-[Amino(Polyethylene Glycol)2000] (sodium salt) (also known as DPPE-PEG(2000)-Amine Na) (Avanti Polar Lipids, Alabaster, A1), Poly(2-methacryloxyethyl trimethylammonium bromide) (Polysciences, Inc., Warrington, Pa.) (also known as S1001), poloxamines such as TETRONIC 908®, also known as POLOXAMINE 908®, which is a tetrafunctional block copolymer derived from sequential addition of propylene oxide and ethylene oxide to ethylenediamine (BASF Wyandotte Corporation, Parsippany, N.J.), lysozyme, long-chain polymers such as alginic acid, carrageenan (FMC Corp.), and POLYOX (Dow, Midland, Mich.).

Other useful cationic stabilizers include, but are not limited to, cationic lipids, sulfonium, phosphonium, and quaternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, C12-15dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy) ammonium chloride or bromide, N-alkyl (C12-18)dimethylbenzyl ammonium chloride, N-alkyl (C14-18)dimethyl-benzyl ammonium chloride, N-tetradecylidmethylbenzyl ammonium chloride monohydrate, dimethyl didecyl ammonium chloride, N-alkyl and (C12-14) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl(C12-14) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, C12, C15, C17 trimethyl ammonium bromides, dodecylbenzyl triethyl ammonium chloride, polydiallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUAT™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly[diallyl dimethylammonium chloride] and poly-[N-methyl vinyl pyridinium chloride]; and cationic guar.

Such exemplary cationic surfactants or surface stabilizers and other useful cationic surfactants or surface stabilizers are described in J. Cross and E. Singer, Cationic Surfactants: Analytical and Biological Evaluation (Marcel Dekker, 1994); P. and D. Rubingh (Editor), Cationic Surfactants: Physical Chemistry (Marcel Dekker, 1991); and J. Richmond, Cationic Surfactants: Organic Chemistry, (Marcel Dekker, 1990), each of which is incorporated by reference herein in its entirety.

Nonpolymeric cationic surfactants or surface stabilizers are any nonpolymeric compound, such as benzalkonium chloride, a carbonium compound, a phosphonium compound, an oxonium compound, a halonium compound, a cationic organometallic compound, a quaternary phosphorous compound, a pyridinium compound, an anilinium compound, an ammonium compound, a hydroxylammonium compound, a primary ammonium compound, a secondary ammonium compound, a tertiary ammonium compound, and quaternary ammonium compounds of the formula NR1R2R3R4(+). For compounds of the formula NR1R2R3R4(+): (i) none of R1—R4 are CH3; (ii) one of R1-R4 is CH3; (iii) three of R1-R4 are CH3; (iv) all of R1-R4 are CH3; (v) two of R1-R4 are CH3, one of R1-R4 is C6H5CH2, and one of R1-R4 is an alkyl chain of seven carbon atoms or less; (vi) two of R1-R4 are CH3, one of R1-R4 is C6H5CH2, and one of R1-R4 is an alkyl chain of nineteen carbon atoms or more; (vii) two of R1-R4 are CH3 and one of R1-R4 is the group C6H5 (CH2)n, where n>1; (viii) two of R1-R4 are CH3, one of R1-R4 is C6H5CH2, and one of R1-R4 comprises at least one heteroatom; (ix) two of R1-R4 are CH3, one of R1-R4 is C6H5CH2, and one of R1-R4 comprises at least one halogen; (x) two of R1-R4 are CH3, one of R1-R4 is C6H5CH2, and one of R1-R4 comprises at least one cyclic fragment; (xi) two of R1-R4 are CH3 and one of R1-R4 is a phenyl ring; or (xii) two of R1-R4 are CH3 and two of R1-R4 are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), di stearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Most of these surfactants or surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference.

The surfactants or surface stabilizers are commercially available and/or can be prepared by techniques known in the art.

Preferably, the surface of the subject microparticle or nanoparticle is composed of a material that minimizes nonspecific or unwanted biological interactions between the particle surface and the interstitium, e.g., the particle surface may be coated with a material to prevent or decrease non-specific interactions. Steric stabilization by coating particles with hydrophilic layers such as poly(ethylene glycol) (PEG) and its copolymers such as PLURONICS (including copolymers of poly(ethylene glycol)-bl-poly(propylene glycol)-bl-poly(ethylene glycol)) may reduce the non-specific interactions with proteins of the interstitium as demonstrated by improved lymphatic uptake following subcutaneous injections.

7. Particle Sizes

The size of the subject microparticles and nanoparticles is from about 1 nm to about 1000 µm, preferably from about 10 nm to about 100 µm, and most preferably from about 20 nm to about 5 µm, and most preferably from about 50 nm to about 2 µm. For example, the microparticles and nanoparticles may have an average size between about 100 and 900 nm, such as about 100, 300, 500, 700, or 900 nm.

As used herein, particle size can be determined by any conventional particle size measuring techniques well known to those skilled in the art. Such techniques include, for example, sedimentation field flow fractionation, photon correlation spectroscopy, light scattering, dynamic light scattering, light diffraction, and disk centrifugation.

8. Additional Components

Preferably, particles of the present invention may also contain additional components. For example, carriers may have imaging agents incorporated or conjugated to the carrier. An example of a carrier nanosphere having an imaging agent that is currently commercially available is the Kodak X-sight nanospheres. Inorganic quantum-confined luminescent nanocrystals, known as quantum dots (QDs), have emerged as ideal donors in FRET applications: their high quantum yield and tunable size-dependent Stokes Shifts permit different sizes to emit from blue to infrared when excited at a single ultraviolet wavelength. (Bruchez et al., *Science*, 1998, 281:2013; Niemeyer, C. M., *Angew. Chem. Int. Ed.*, 2003, 42:5796; Waggoner, A. *Methods Enzymol.*, 1995, 246:362; Brus, L. E., *J. Chem. Phys.*, 1993, 79, 5566). Quantum dots, such as hybrid organic/inorganic quantum dots based on a class of polymers known as dendrimers, may be used in biological labeling, imaging, and optical biosensing systems (Lemon et al., *J. Am. Chem. Soc.*, 2000, 122:12886). Unlike the traditional synthesis of inorganic quantum dots, the synthesis of these hybrid quantum dot nanoparticles does not require high temperatures or highly toxic, unstable reagents. (Etienne et al., *Appl. Phys. Lett.*, 87:181913, 2005).

9. API

Another aspect of the invention provides a composition comprising the subject microparticles or nanoparticles having negative surface charges, wherein the composition is prepared according to any one of the subject methods described herein or combinations thereof.

The composition can be free from other active pharmaceutical ingredients or API, such as attached peptide or antigenic moieties. It is understood that an API can be substituted with non-therapeutic compounds, such as diagnostic, agricultural or chemical agents. Therefore, in each instance where the term API is used, it shall be understood that the term "active agent," including diagnostic, agricultural or chemical agents can be used in lieu thereof.

The composition can comprise an API, and the API can be covalently or ionically attached to the surface of the microparticles or nanoparticles via covalent bonds, such as a bond formed between an amide group of a protein and a carboxyl group on the surface of the microparticle or nanoparticle. The API can also be encapsulated within the microparticles or nanoparticles.

The amount of the API can be about 0.01-50% (w/w) of the microparticle or nanoparticle, or about 0.05-25%, about 0.1-10%, about 0.2-5%, 0.5-3%, 1-5%, or 2-5% (w/w) of the microparticle or nanoparticle.

Preferably, the composition comprises, in place of an API or in addition thereto, a targeting moiety, such as a peptide or protein ligand or domain, covalently attached to the surface of the microparticles or nanoparticles, which targeting moiety specifically or preferentially binds to a target site (such as a cell surface receptor or binding partner for the targeting moiety), such that the micro- or nanoparticle bearing such a targeting moiety will be specifically or preferentially directed to the target site in vivo. The targeting moiety bearing micro- or nanoparticle may further comprise an API that is encapsulated or embedded within the micro- or nanoparticle that can be released or otherwise effective at the target site. In fact, the sulfate polymer (e.g., fucoidan or sialic acid) can itself be a targeting moiety for cancer cells.

By having targeting moieties, target specific nanoparticles are able to efficiently bind to or otherwise associate with a biological entity, for example, a membrane component or cell surface receptor. Targeting of a therapeutic agent (e.g., to a particular tissue or cell type, to a specific diseased tissue but not to normal tissue, etc.) is desirable for the treatment of tissue specific diseases such as cancer (e.g. prostate cancer). For example, in contrast to systemic delivery of a cytotoxic anti-cancer agent, targeted delivery could prevent the agent from killing healthy cells. Additionally, targeted delivery would allow for the administration of a lower dose of the agent, which could reduce the undesirable side effects commonly associated with traditional chemotherapy. As discussed above, the target specificity of the nanoparticles of the invention will be maximized by optimizing the ligand density on the nanoparticle. Targeting moieties can be covalently bound to the surface of the nanoparticle or microparticle. For example, targeting moieties can be covalently bound to the sulfate polymer (e.g., by coupling one or more carboxylic acid moieties), the PLGA/PLA (e.g., via a polymer terminal) or by incorporating yet another molecule or polymer into the interpenetrating network. For example, the targeting moiety can be covalently linked to a polyethyleneglycol (PEG) molecule or PLGA-PEG diblock and added to the emulsion with the sulfate polymer.

For example, a targeting moiety can be a moiety able to bind to or otherwise associate with a biological entity, for example, a membrane component, a cell surface receptor, prostate specific membrane antigen, or the like. In the case of the instant invention, the targeting moiety is a low-molecular weight PSMA ligand. The term "bind" or "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to molecules, such as polynucleotides, that are able to bind to or recognize a binding partner (or a limited number of binding partners) to a substantially higher degree than to other, similar biological entities. In one set of embodiments, the targeting moiety has an affinity (as measured via a disassociation constant) of less than about 1 micromolar, at least about 10 micromolar, or at least about 100 micromolar.

In preferred embodiments, the targeting moiety of the invention is a small molecule. In certain embodiments, the term "small molecule" refers to organic compounds, whether naturally-occurring or artificially created (e.g., via chemical synthesis) that have relatively low molecular weight and that are not proteins, polypeptides, or nucleic acids. Small molecules typically have multiple carbon-carbon bonds. In certain embodiments, small molecules are less than about 2000 g/mol in size. In some embodiments, small molecules are less than about 1500 g/mol or less than about 1000 g/mol. In some embodiments, small molecules are less than about 800 g/mol or less than about 500 g/mol.

In particularly preferred embodiments, the small molecule targeting moiety targets prostate cancer tumors, and, in particular, the small molecule targeting moiety is a PSMA peptidase inhibitor. These moieties are also referred to herein as "low-molecular weight PSMA ligands." When compared with expression in normal tissues, expression of prostate specific membrane antigen (PSMA) is at least 10-fold overexpressed in malignant prostate relative to normal tissue, and the level of PSMA expression is further up-regulated as the disease progresses into metastatic phases (Silver et al. 1997, Clin. Cancer Res., 3:81), as described in US Patent Publication 2014/0235706.

In some embodiments, small molecule targeting moieties that may be used to target cells associated with prostate cancer tumors include PSMA peptidase inhibitors such as 2-PMPA, GPI5232, VA-033, phenylalkylphosphonamidates (Jackson et al., 2001, Curr. Med. Chem., 8:949; Bennett et al, 1998, J. Am. Chem. Soc., 120:12139; Jackson et al., 2001, J. Med. Chem., 44:4170; Tsulcarnoto et al, 2002, Bioorg. Med. Chem. Lett., 12:2189; Tang et al., 2003, Biochem. Biophys. Res. Commun., 307:8; Oliver et al., 2003, Bioorg. Med. Chem., 11:4455; and Maung et al., 2004, Bioorg. Med. Chem., 12:4969), and/or analogs and derivatives thereof. In some embodiments, small molecule targeting moieties that may be used to target cells associated with prostate cancer tumors include thiol and indole thiol derivatives, such as 2-MPPA and 3-(2-mercaptoethyl)-1H-indole-2-carboxylic acid derivatives (Majer et al., 2003, J. Med. Chem., 46:1989; and U.S. Patent Publication 2005/0080128). In some embodiments, small molecule targeting moieties that may be used to target cells associated with prostate cancer tumors include hydroxamate derivatives (Stoermer et al., 2003, Bioorg. Med. Chem. Lett., 13:2097).

In some embodiments, small molecule targeting moieties that may be used to target cells associated with prostate cancer tumors include PBDA- and urea-based inhibitors, such as ZJ 43, ZJ 11, ZJ 17, ZJ 38 (Nan et al. 2000, J. Med. Chem., 43:772; and Kozikowski et al., 2004, J. Med. Chem., 47:1729), and/or and analogs and derivatives thereof. In some embodiments, small molecule targeting moieties that may be used to target cells associated with prostate cancer tumors include putrescine, spermine, and spermidine, androgen receptor targeting agents (ARTAs), such as those described in U.S. Pat. Nos. 7,026,500; 7,022,870; 6,998,500; 6,995,284; 6,838,484; 6,569,896; 6,492,554; and in U.S. Patent Publications 2006/0287547; 2006/0276540; 2006/0258628; 2006/0241180; 2006/0183931; 2006/0035966; 2006/0009529; 2006/0004042; 2005/0033074; 2004/0260108; 2004/0260092; 2004/0167103; 2004/0147550; 2004/0147489; 2004/0087810; 2004/0067979; 2004/0052727; 2004/0029913; 2004/0014975; 2003/0232792; 2003/0232013; 2003/0225040; 2003/0162761; 2004/0087810; 2003/0022868; 2002/0173495; 2002/0099096; 2002/0099036. A related aspect of the invention provides a pharmaceutical composition comprising the subject composition, and a pharmaceutically accepted carrier or excipient. Pharmaceutical compositions are described below in more details in a separate section.

The API can be water-soluble or have relatively poor water-solubility. For example, a poorly water-soluble API may be dissolved in the same first solvent used to dissolve PLGA, or be dissolved in a suitable solvent (that may be the same or different from the first solvent) to form an API solution, before the API solution is mixed with the first solvent comprising PLGA, such that the API and PLGA both remain in the resulting solution.

A water-soluble API may be first dissolved in its own solvent (that may be the same or different from the $2^{nd}$ solvent) to form an API solution, before the API solution is added to the second solvent.

An API or therapeutic agent can include a wide variety of different compounds, including chemical compounds and mixtures of chemical compounds, e.g., small organic or inorganic molecules; saccharine; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof. Preferably, the therapeutic agent is a small molecule.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary therapeutic agents include, but are not limited to, those approved by the FDA, subject to a new drug application with the FDA, in clinical trials or in preclinical research.

APIs, or therapeutic agents, include the herein disclosed categories and specific examples. It is not intended that the category be limited by the specific examples. Those of ordinary skill in the art will recognize also numerous other compounds that fall within the categories and that are useful according to the present disclosure. Examples include a radiosensitizer, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an antiparkinsonian agent, an antianginal/antihypertensive agent, an anticoagulant agent, an antiplatelet agent, a sedative, an anxiolytic agent, a peptidic agent, a biopolymeric agent, an antineoplastic agent, a laxative, an antidiarrheal agent, an antimicrobial agent, an antifungal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetaminophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and diisopyramide phosphate; antiparkinsonian agents, such as dopamine, L-Dopa/Carbidopa, selegiline, dihydroergocryptine, pergolide, lisuride, apomorphine, and bromocryptine; anti-angina agents and antihypertensive agents such as isosorbide mononitrate, isosorbide dinitrate, propranolol, atenolol and verapamil; anticoagulant and antiplatelet agents such as Coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hydrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides.

Examples of suitable APIs include infliximab, etanercept, bevacizumab, ranibizumab, adalimumab, certolizumab pegol, golimumab, Interleukin 1 (IL-1) blockers such as anakinra, T cell costimulation blockers such as abatacept, Interleukin 6 (IL-6) blockers such as tocilizumab; Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/.beta.2 blockers such as Anti-lymphotoxin alpha (LTa) or anti-VEGF agents and the like.

The term "API" is used herein for convenience. It is understood that the term can be replaced within this specification by the terms biomolecule, protein and nucleic acid as if specifically recited in each instance.

The present invention is particularly applicable to the administration of anti-cancer agents. For example, the agent can be a DNA demethylating agents 5-azacytidine (azacitidine) or 5-aza-2'-deoxycytidine (decitabine), (Cytarabine or ara-C); pseudoiso-cytidine (psi ICR); 5-fluoro-2'-deoxycytidine (FCdR); 2'-deoxy-2',2'-difluorocytidine (Gemcitabine); 5-aza-2'-deoxy-2',2'-difluorocytidine; 5-aza-2'-deoxy-2'-fluorocytidine; Zebularine; 2',3'-dideoxy-5-fluoro-3'-thiacytidine (Emtriva); 2'-cyclocytidine (Ancitabine); Fazarabine or ara-AC; 6-azacytidine (6-aza-CR); 5,6-dihydro-5-azacytidine (dH-aza-CR); N.sup.4-pentyloxy-carbonyl-5'-deoxy-5-fluorocytidine (Capecitabine); $N^4$-octadecyl-cytarabine; or elaidic acid cytarabine. The cytidine analog can also be structurally related to cytidine or deoxycytidine and functionally mimics and/or antagonizes the action of cytidine or deoxycytidine. The agents can also include 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celecoxib, chlorambucil, cisplatinum, COX-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, DM1, DM3, DM4, doxorubicin, 2-pyrrolinodoxorubicine (2-PDox), a pro-drug form of 2-PDox (pro-2-PDox), cyano-morpholino doxorubicin, doxorubicin glucuronide, endostatin, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, monomethylauristatin F (MMAF), monomethylauristatin D (MMAD), monomethyl-auristatin E (MMAE), navelbine, neratinib, nilotinib, nitrosurea, olaparib, plicamycin, procarbazine, paclitaxel, PCI-32765, pentostatin, PSI-341, raloxifene, semustine, SN-38, sorafenib, streptozocin, SU11248, sunitinib, tamoxifen, temazolomide, transplatinum, thalidomide, thioguanine, thiotepa, teniposide, topotecan, uracil mustard, vatalanib, vinorelbine, vinblastine, vincristine, *Vinca* alkaloids and ZD1839 or a pharmaceutically acceptable salt thereof.

The anticancer agents include, but are not limited to, an inhibitor, agonist, antagonist, ligand, modulator, stimulator, blocker, activator or suppressor of a gene, ligand, receptor, protein, factor such as an adenosine receptor (such as A2B, A2a, A3), Abelson murine leukemia viral oncogene homolog 1 gene (ABL, such as ABL1), Acetyl-CoA carboxylase (such as ACC1/2), adrenocorticotropic hormone receptor (ACTH), activated CDC kinase (ACK, such as ACK1), Adenosine deaminase, Adenylate cyclase, ADP ribosyl cyclase-1, Aerolysin, Angiotensinogen (AGT) gene, murine thymoma viral oncogene homolog 1 (AKT) protein kinase (such as AKT1, AKT2, AKT3), AKT1 gene, Alkaline phosphatase, Alpha 1 adrenoceptor, Alpha 2 adrenoceptor, Alpha-ketoglutarate dehydrogenase (KGDH), Aminopeptidase N, Arginine deiminase, Beta adrenoceptor, Anaplastic lymphoma kinase receptor, anaplastic lymphoma kinase (ALK, such as ALK1), Alk-5 protein kinase, AMP activated protein kinase, Androgen receptor, Angiopoietin (such as ligand-1, ligand-2), apolipoprotein A-I (APOA1) gene, apoptosis signal-regulating kinase (ASK, such as ASK1), Apoptosis inducing factor, apoptosis protein (such as 1, 2), Arginase (I), asparaginase, Asteroid homolog 1 (ASTE1) gene, ataxia telangiectasia and Rad 3 related (ATR) serine/threonine protein kinase, Axl tyrosine kinase receptor, Aromatase, Aurora protein kinase (such as 1, 2), Basigin, BCR (breakpoint cluster region) protein and gene, B-cell lymphoma 2 (BCL2) gene, Bcl2 protein, Bcl2 binding component 3, BCL2L11 gene, Baculoviral IAP repeat containing 5 (BIRCS) gene, B-Raf proto-oncogene (BRAF), Brc-Abl tyrosine kinase, Beta-catenin, B-lymphocyte antigen CD19, B-lymphocyte antigen CD20, B-lymphocyte stimulator ligand, B-lymphocyte cell adhesion molecule, Bone morphogenetic protein-10 ligand, Bone morphogenetic protein-9 ligand modulator, Brachyury protein, Bradykinin receptor, Bruton's tyrosine kinase (BTK), Bromodomain and external domain (BET) bromodomain containing protein (such as BRD2, BRD3, BRD4), Calmodulin, calmodulin-dependent protein kinase (CaMK, such as CAMKII), Cancer testis antigen 2, Cancer testis antigen NY-ESO-1, Cannabinoid receptor (such as CB1, CB2), Carbonic anhydrase, caspase 8 apoptosis-related cysteine peptidase CASP8-FADD-like regulator, Caspase (such as caspase-3, caspase-7, Caspase-9), Caspase recruitment domain protein-15, Cathepsin G, chemokine (C—C motif) receptor (such as CCR2, CCR4, CCR5), CCR5 gene, Chemokine CC21 ligand, cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e, CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; Chorionic gonadotropin, Cyclin G1, Cyclin D1, cyclin-dependent kinases (CDK, such as CDK1, CDK1B, CDK2-9), casein kinase (CK, such as CM, CMI), c-Kit (tyrosine-protein kinase Kit or CD117), c-Met (hepatocyte growth factor receptor (HGFR)), CDK-activating kinase (CAK), Checkpoint kinase (such as CHK1, CHK2), Cholecystokinin CCK2 receptor, Claudin (such as 6, 18), Clusterin, Complement C3, COP9 signalosome subunit 5, CSF-1 (colony-stimulating factor 1 receptor), CSF2 gene, clusterin (CLU) gene, Connective tissue growth factor, cyclooxygenase (such as 1, 2), cancer/testis antigen 1B (CTAG1) gene, CTLA-4 (cytotoxic T-lymphocyte protein 4) receptor, CYP2B1 gene, Cysteine palmitoyltransferase porcupine, cytokine signalling-1, cytokine signalling-3, Cytochrome P450 11B2, Cytochrome P450 reductase, cytochrome P450 3A4, cytochrome P450 17A1, Cytochrome P450 17, Cytochrome P450 2D6, (provided they anticancer or cytrochrome modifying agents are something other than cobicistat), Cytoplasmic isocitrate dehydrogenase, Cytosine deaminase, cytosine DNA methyltransferase, cytotoxic T-lymphocyte protein-4, chemokine (C—X—C motif) receptor (such as CXCR4, CXCR1 and CXCR2), Delta-like protein ligand (such as 3, 4), Deoxyribonuclease, Dickkopf-1 ligand, Dihydropyrimidine dehydrogenase, DNA binding protein (such as HU-beta), DNA dependent protein kinase, DNA gyrase, DNA methyltransferase, DNA polymerase (such as alpha), DNA primase, discoidin domain receptor (DDR, such as DDR1), DDR2 gene, dihydrofolate reductase (DHFR), Dipeptidyl peptidase IV, L-dopachrome tautomerase, dUTP pyrophosphatase, echinoderm microtubule like protein 4, epidermal growth factor receptor (EGFR) gene, EGFR tyrosine kinase receptor, Eukaryotic translation initiation factor 5A (EIFSA) gene, Elastase, Elongation factor 1 alpha 2, Elongation factor 2, Endoglin, Endonuclease, Endoplasmin, Endosialin, Endostatin, endothelin (such as ET-A, ET-B), Enhancer of zeste homolog 2 (EZH2), epidermal growth factor, epidermal growth factor receptors (EGFR), Epithelial cell adhesion molecule (EpCAM), Ephrin (EPH) tyrosine kinase (such as Epha3, Ephb4), Ephrin B2 ligand, Epigen, Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, Extracellular signal-regulated kinases (ERK), E-selectin, Estradiol 17 beta dehydrogenase, Estrogen receptor (such as alpha, beta), Estrogen related receptor, Exportin 1, Extracellular signal related kinase (such as 1, 2), Factor (such as Xa, VIIa), Fas ligand, Fatty acid synthase, Ferritin, focal adhesion kinase (FAK, such as FAK2), fibroblast growth factor (FGF, such as FGF1, FGF2, FGF4), FGF-2 ligand, FGF-5 ligand, Fibronectin, Fms-related tyrosine kinase 3 (Flt3), farnesoid x receptor (FXR), Folate, Folate transporter 1, Folate receptor (such as alpha), folate hydrolase prostate-specific membrane antigen 1 (FOLH1), paired basic amino acid cleaving enzyme (FURIN), FYN tyrosine kinase, Galactosyltransferase, Galectin-3, glucocorticoid-induced TNFR-related protein GITR receptor, Glucocorticoid, Beta-glucuronidase, Glutamate carboxypeptidase II, glutaminase, Glutathione S-transferase P, Glypican 3 (GPC3), glycogen synthase kinase (GSK, such as 3-beta), Granulocyte-colony stimulating factor (GCSF) ligand, Granulocyte macrophage colony stimulating factor (GM-CSF) receptor, gonadotropin-releasing hormone (GNRH), growth factor receptor-bound protein 2 (GRB2), molecular chaperone groEL2 gene, Grp78 (78 kDa glucose-regulated protein) calcium binding protein, Imprinted Maternally Expressed Transcript (H19) gene, Heat stable enterotoxin receptor, Heparanase, Hepatocyte growth factor, Heat shock protein gene, Heat shock protein (such as 27, 70, 90 alpha, beta), Hedgehog protein, HERV-H LTR associating protein 2, Hexose kinase, tyrosine-protein kinase HCK, Histamine H2 receptor, histone deacetylase (HDAC, such as 1, 2, 3, 6, 10, 11), Histone H1, Histone H3, Histone methyltransferase (DOT1L), Human leukocyte antigen (HLA), HLA class I antigen (A-2 alpha), HLA class II antigen, Homeobox protein NANOG, mitogen-activated protein kinase kinase kinase kinase 1 (MAP4K1, HPK1), HSPB1 gene, Human papillomavirus (such as E6, E7) protein, Hyaluronidase, Hyaluronic acid, Hypoxia inducible factor-1 alpha, Intercellular adhesion molecule 1 (ICAM-1), immunoglobulin (such as G, G1, G2, K, M), indoleamine 2,3-dioxygenase (IDO, such as IDO1), indoleamine pyrrole 2,3-dioxygenase 1 inhibitor, I-Kappa-B kinase (IKK, such as IKKβ.epsilon.), Immunoglobulin Fc receptor, Immunoglobulin gamma Fc receptor (such as I, III, IIIA), Interleukin 1 ligand, interleukin 2 ligand, Interleukin-2, IL-2 gene, IL-1 alpha, IL-1 beta, IL-2, IL-2 receptor alpha subunit, IL-3 receptor, IL-4, IL-6, IL-7, IL-8, IL-12, IL-15, IL-12 gene, IL-17, Interleukin 13 receptor alpha 2, Interleukin-29 ligand, interleukin-1 receptor-associated kinase 4 (IRAK4), Insulin-like growth factor (such as 1, 2), insulin receptor, Integrin alpha-V/beta-3, Integrin alpha-V/beta-5, Integrin alpha-V/beta-6, Integrin alpha-5/beta-1, Integrin alpha-4/beta-1, integrin alpha-4/beta-7, Interferon inducible protein absent in melanoma 2 (AIM2), interferon (such as alpha, alpha 2, beta, gamma), interferon type I receptor, isocitrate dehydrogenase (such as IDH1, IDH2), Janus kinase (JAK, such as JAK1, JAK2), Jun N terminal kinase, Kinase insert domain receptor (KDR), Killer cell Ig like receptor, Kisspeptin (KISS-1) receptor, v-kit Hardy-Zuckerman 4 feline sarcoma viral oncogene homolog (KIT) tyrosine kinase, KIT gene, Kinesin-like protein KIF11, kallikrein-related peptidase 3 (KLK3) gene, Kirsten rat sarcoma viral oncogene homolog (KRAS) gene, lactoferrin, lymphocyte activation gene 3 protein (LAG-3), lysosomal-associated membrane protein family (LAMP) gene, Lanosterol-14 demethylase, LDL receptor related protein-1, Leukotriene A4 hydrolase, Listeriolysin, L-Selectin, Luteinizing hormone receptor, Lyase, Lymphocyte antigen 75, lysine demethylases (such as KDM1, KDM2, KDM4, KDM5, KDM6, A/B/C/D), Lymphocyte function antigen-3 receptor, lymphocyte-specific protein tyrosine kinase (LCK), Lymphotactin, Lyn (Lck/Yes novel) tyrosine kinase, Lysophosphatidate-1 receptor, lysyl oxidase protein (LOX), lysyl oxidase-like protein (LOXL, such as LOXL2), Lysyl oxidase homolog 2, Macrophage migration inhibitory fact, melanoma antigen family A3 (MAGEA3) gene, MAGEC1 gene, MAGEC2 gene, Major vault protein, myristoylated alanine-rich protein kinase C substrate (MARCKS) protein, Melan-A (MART-1) melanoma antigen, Mas-related G-protein coupled receptor, matrix metalloprotease (MMP, such as MMP2, MMP9), myeloid cell leukemia 1 (MCL1) gene, Mcl-1 differentiation protein, macrophage colony-stimulating factor (MCSF) ligand, Melanoma associated antigen (such as 1, 2, 3, 6), melanocyte stimulating hormone ligand, Melanocyte protein Pmel 17, Membrane copper amine oxidase, Mesothelin, Metabotropic glutamate receptor 1, mitogen-activated protein kinase (MEK, such as MEK1, MEK2), Hepatocyte growth factor receptor (MET) gene, MET tyrosine kinase, methionine aminopeptidase-2, mitogen-activate protein kinase (MAPK), Mdm2 p53-binding protein, Mdm4 protein, Metalloreductase STEAP1 (six transmembrane epithelial antigen of the prostate 1), Metastin, Methyltransferase, Mitochondrial 3 ketoacyl CoA thiolase, MAPK-activated protein kinase (such as MK2), mTOR (mechanistic target of rapamycin (serine/threonine kinase), mTOR complex (such as 1, 2), mucin (such as 1, 5A, 16), mut T homolog (MTH, such as MTH1), Myc proto-oncogene protein, NAD ADP ribosyltransferase, natriuretic peptide receptor C, Neural cell adhesion molecule 1, Neurokinin receptor, Neuropilin 2, Nitric oxide synthase, Nuclear Factor (NF) kappa B, NF kappa B activating protein, Neurokinin 1 (NK1) receptor, NK cell receptor, NK3 receptor, NKG2 A B activating NK receptor, NIMA-related kinase 9 (NEK9), Noradrenaline transporter, Notch (such as Notch-2 receptor, Notch-3 receptor), nucleophosmin-anaplastic lymphoma kinase (NPM-ALK), 2,5-oligoadenylate synthetase, Nuclear erythroid 2-related factor 2, Nucleolin, Nucleophosmin, O-methylguanine DNA methyltransferase, Ornithine decarboxylase, Orotate phosphoribosyltransferase, orphan nuclear hormone receptor NR4A1, Opioid receptor (such as delta), Osteocalcin, Osteoclast differentiation factor, Osteopontin, OX-40 (tumor necrosis factor receptor superfamily member 4 TNFRSF4, or CD134) receptor, 2 oxoglutarate dehydrogenase, purinergic receptor P2X ligand gated ion channel 7 (P2X7), Parathyroid hormone ligand, p53 tumor suppressor protein, P3 protein, Programmed cell death 1 (PD-1), Protooncogene serine/threonine-protein kinase (PIM, such as PIM-1, PIM-2, PIM-3), Poly ADP ribose polymerase (PARP, such as PARP1, 2 and 3), p38 kinase, p38 MAP kinase, platelet-derived growth factor (PDGF, such as alpha, beta), P-Glycoprotein (such as 1), Platelet-derived growth factor (PDGF, such as alpha, beta), PKN3 gene, P-Selectin, phosphatidylinositol 3-kinase (PI3K), phosphoinositide-3 kinase (PI3K such as alpha, delta, gamma), phosphorylase kinase (PK), placenta growth factor, Pleiotropic drug resistance transporter, Plexin B1, Polo-like kinase 1, peroxisome proliferator-activated receptors (PPAR, such as alpha, delta, gamma), Preferentially expressed antigen in melanoma (PRAME) gene, Probable transcription factor PML, Programmed cell death ligand 1 inhibitor (PD-L1), Progesterone receptor, prostate specific antigen, Prostatic acid phosphatase, Prostanoid receptor (EP4), proteasome, Protein farnesyltransferase, protein kinase (PK, such as A, B, C), Protein E7, protein tyrosine kinase, Protein tyrosine phosphatase beta, polo-like kinase (PLK), PLK1 gene, Prenylbinding protein (PrPB), protoporphyrinogen oxidase, Prosaposin (PSAP) gene, phosphatase and tensin homolog (PTEN), Purine nucleoside phosphorylase, Pyruvate kinase (PYK), Pyruvate dehydrogenase (PDH), Pyruvate dehydrogenase kinase, Raf protein kinase (such as 1, B), RAF1 gene, Ras GTPase, Ras gene, 5-Alpha-reductase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS protooncogene 1, receptor tyrosine kinase) gene, Ros1 tyrosine kinase, Runt-related transcription factor 3, S100 calcium binding protein A9, Sarco endoplasmic calcium ATPase, Gamma-secretase, Secreted frizzled related protein-2, Semaphorin-4D, SL cytokine ligand, Serine protease, Signaling lymphocytic activation molecule (SLAM) family member 7, spleen tyrosine kinase (SYK), Src tyrosine kinase, tumor progression locus 2 (TPL2), serine/threonine kinase (STK), signal transduction and transcription (STAT, such as STAT-1, STAT-3, STAT-5), Second mitochondria-derived activator of caspases (SMAC) protein, smoothened (SMO) receptor, Sodium phosphate cotransporter 2B, Sodium iodide cotransporter, Somatostatin receptor (such as 1, 2, 3, 4, 5), Sonic hedgehog protein, Specific protein 1 (Sp1) transcription factor, Sphingomyelin synthase, Sphingosine-1-phosphate receptor-1, Sphingosine kinase (such as 1, 2), SRC gene, STAT3 gene, six-transmembrane epithelial antigen of the prostate (STEAP) gene, Steroid sulfatase, stimulator of interferon genes protein, Stimulator of interferon genes (STING) receptor, Stromal cell-derived factor 1 ligand, SUMO (small ubiquitin-like modifier), Superoxide dismutase, Survivin protein, Synapsin 3, Syndecan-1, Synuclein alpha, serine/threonine-protein kinase (TBK, such as TBK1), TATA box-binding protein-associated factor RNA polymerase I subunit B (TAF1B) gene, T-cell surface glycoprotein CD8, T-cell CD3 glycoprotein zeta chain, T-cell differentiation antigen CD6, T cell surface glycoprotein CD28, Tec protein tyrosine kinase, Tek tyrosine kinase receptor, telomerase, Tenascin, Telomerase reverse transcriptase (TERT) gene, Transforming growth factor (TGF, such as beta) kinase, TGF beta 2 ligand, T-cell immunoglobulin and mucin-domain containing-3 (TIM-3), Tissue factor, Tumor necrosis factor (TNF, such as alpha, beta), TNF related apoptosis inducing ligand, TNFR1 associated death domain protein, TNFSF9 gene, TNFSF11 gene, trophoblast glycoprotein (TPBG) gene, Transferrin, Tropomyosin receptor kinase (Trk) receptor (such as TrkA, TrkB, TrkC), Trophoblast glycoprotein, Thymidylate synthase, Tyrosine kinase with immunoglobulin-like and EGF-like domains (TIE) receptor, Toll-like receptor (TLR such as 1-13), topoisomerase (such as I, II, III), Tumor protein 53 (TP53) gene, Transcription factor, Transferase, Transforming growth factor TGF-.beta. receptor kinase, Transglutaminase, Translocation associated protein, Transmembrane glycoprotein NMB, Tumor necrosis factor 13C receptor, Thymidine kinase, Thymidine phosphorylase, Thymidylate synthase, Thymosin (such as alpha 1), Thyroid hormone receptor, Trop-2 calcium signal transducer, Thyroid stimulating hormone receptor, Tryptophan 5-hydroxylase, Tyrosinase, tyrosine kinase (TK), Tyrosine kinase receptor, Tyrosine protein kinase ABL1 inhibitor, tank-binding kinase (TBK), Thrombopoietin receptor, TNF-related apoptosis-inducing ligand (TRAIL) receptor, Tubulin, Tumor suppressor candidate 2 (TUSC2) gene, Tyrosine hydroxylase, Ubiquitin-conjugating enzyme E2I (UBE2I, UBC9), Ubiquitin, Ubiquitin carboxyl hydrolase isozyme L5, Ubiquitin thioesterase-14, Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Protooncogene tyrosine-protein kinase Yes, Wee-1 protein kinase, Wilms' tumor protein, Wilms' tumor antigen 1, X-linked inhibitor of apoptosis protein, Zinc finger protein transcription factor or any combination thereof.

The anticancer agent includes agents defined by their mechanism of action or class, including: anti-metabolites/anti-cancer agents such as pyrimidine analogs floxuridine, capecitabine, cytarabine, CPX-351 (liposomal cytarabine, daunorubicin), TAS-118; purine analogs, folate antagonists (such as pralatrexate), and related inhibitors; antiproliferative/antimitotic agents including natural products such as *Vinca* alkaloid (vinblastine, vincristine) and microtubule such as taxane (paclitaxel, docetaxel), vinblastin, nocodazole, epothilones, vinorelbine) (NAVELBINE), and epipodophyllotoxins (etoposide, teniposide); DNA damaging agents such as actinomycin, amsacrine, busulfan, carboplatin, chlorambucil, cisplatin, cyclophosphamide) (CYTOXAN), dactinomycin, daunorubicin, doxorubicin, epirubicin, iphosphamide, melphalan, merchlorethamine, mitomycin C, mitoxantrone, nitrosourea, procarbazine, taxol, Taxotere, teniposide, etoposide, and triethylenethiophosphoramide; DNA-hypomethylating agent such as guadecitabine (SGI-110) antibiotics such as dactinomycin, daunorubicin, doxorubicin, idarubicin, anthracyclines, mitoxantrone, bleomycins, plicamycin (mithramycin), and; enzymes such as L-asparaginase which systemically metabolizes L-asparagine and deprives cells which do not have the capacity to synthesize their own asparagine; anti-platelet agents; a DNAi oligonucleotide targeting Bcl-2 such as PNT2258; agents that activate or reactivate latent human immunodeficiency virus (HIV) such as panobinostat or romidepsin asparaginase stimulators, such as crisantaspase (Erwinase®) and GRASPA (ERY-001, ERY-ASP); pan-Trk, ROS1 and ALK inhibitors such as entrectinib anaplastic lymphoma kinase (ALK) inhibitors such as alectinib anti-proliferative/antimitotic alkylating agents such as nitrogen mustards cyclophosphamide and analogs (melphalan, chlorambucil, hexamethylmelamine, and thiotepa), alkyl nitrosoureas (carmustine) and analogs, streptozocin, and triazenes (dacarbazine); antiproliferative/antimitotic antimetabolites such as folic acid analogs (methotrexate); platinum coordination complexes (cisplatin, oxiloplatinim, and carboplatin), procarbazine, hydroxyurea, mitotane, and aminoglutethimide; hormones, hormone analogs (estrogen, tamoxifen, goserelin, bicalutamide, and nilutamide), and aromatase inhibitors (letrozole and anastrozole); anticoagulants such as heparin, synthetic heparin salts, and other inhibitors of thrombin; fibrinolytic agents such as tissue plasminogen activator, streptokinase, urokinase, aspirin, dipyridamole, ticlopidine, and clopidogrel; antimigratory agents; antisecretory agents (breveldin); immunosuppresives tacrolimus, sirolimus, azathioprine, and mycophenolate; compounds (TNP-470, genistein) and growth factor inhibitors (vascular endothelial growth factor inhibitors, and fibroblast growth factor inhibitors such as FPA14; angiotensin receptor blockers, nitric oxide donors; antisense oligonucleotides, such as AEG35156; DNA interference oligonucleotides, such as PNT2258, AZD-9150 antibodies such as trastuzumab and rituximab; anti-HER3 antibodies, such as LJM716 anti-HER2 antibodies such as margetuximab; anti-HLA-DR antibodies such as IMMU-114; anti-IL-3 antibodies, such as JNJ-56022473; anti-OX40 antibodies such as MEDI6469 anti-EphA3 antibodies, such as KB-004; an anti-CD20 antibody such as obinutuzumab; an anti-programmed cell death protein 1 (anti-PD-1) antibody such as nivolumab (OPDIVO, BMS-936558, MDX-1106), pembrolizumab (KEYTRUD, MK-3477, SCH-900475, lambrolizumab, CAS Reg. No. 1374853-91-4), pidilizumab, and anti-programmed death-ligand 1 (anti-PD-L1) antibodies such as BMS-936559, atezolizumab (MPDL3280A), durvalumab (MEDI4736), avelumab (MSB0010718C), and MDX1105-01, CXCR4 antagonists such as BL-8040; CXCR2 antagonist such as AZD-5069; GM-CSF antibodies such as lenzilumab. Selective estrogen receptor downregulator (SERD) such as fulvestrant (Faslodex); a transforming growth factor-beta (TGF-beta) kinase antagonist such as galunisertib; a bispecific antibody such as MM-141 (IGF-1/ErbB3), MM-111 (Erb2/Erb3), JNJ-64052781 (CD19/CD3). Mutant selective EGFR inhibitors, such as PF-06747775, EGF816, ASP8273, ACEA-0010, BI-1482694. Alpha-ketoglutarate dehydrogenase (KGDH) inhibitors such as CPI-613, XPO1 inhibitors such as selinexor (KPT-330). Isocitrate dehydrogenase 2 (IDH2) inhibitors such as enasidenib (AG-221), and IDH1 inhibitors such as AG-120, and AG-881 (IDH1 and IDH2). Agents that target the interleukin-3 receptor (IL-3R) such as SL-401. Arginine deiminase stimulators, such as pegargiminase (ADI-PEG-20) antibody-drug conjugates, such as MLN0264 (anti-GCC, guanylyl cyclase C), T-DM1 (trastuzumab emtansine, Kadcycla), milatuzumab-doxorubicin (hCD74-DOX), brentuximab vedotin, DCDT2980S, polatuzumab vedotin, SGN-CD70A, SGN-CD19A, inotuzumab ozogamicin, lorvotuzumab mertansine, SAR3419, isactuzumab govitecan, anti-claudin-18.2 antibodies such as IMAB362.beta.-catenin inhibitors, such as CWP-291 a CD73 antagonist such as MEDI-9447; c-PIM inhibitors, such as PIM447, a BRAF inhibitor such as dabrafenib, vemurafenib, a sphingosine kinase-2 (SK2) inhibitor such as Yeliva. (ABC294640) cell cycle inhibitors such as selumetinib (MEK1/2), sapacitabine, AKT inhibitors such as MK-2206, ipatasertib, afuresertib, anti-CTLA-4 (cytotoxic T-lymphocyte protein-4) inhibitor such as tremelimumab, c-MET inhibitors, such as AMG-337, savolitinib, tivantinib (ARQ-197), capmatinib, tepotinib inhibitors of CSF1R/KIT and FLT3 such as PLX3397, a kinase inhibitor such as vandetanib; E selectin antagonists such as GMI-1271, differentiation inducers such as tretinoin; epidermal growth factor receptor (EGFR) inhibitors such as osimertinib (AZD-9291) topoisomerase inhibitors (doxorubicin, daunorubicin, dactinomycin, eniposide, epirubicin, etoposide, idarubicin, irinotecan, mitoxantrone, pixantrone, sobuzoxane, topotecan, and irinotecan, MM-398 (liposomal irinotecan), vosaroxin and corticosteroids (cortisone, dexamethasone, hydrocortisone, methylprednisolone, prednisone, and prednisolone); growth factor signal transduction kinase inhibitors; dysfunction inducers; nucleoside analogs such as DFP-10917 Axl inhibitors such as BGB-324; BET inhibitors such as INCB-054329, PARP inhibitors such as olaparib, rucaparib, veliparib, Proteasome inhibitors such as ixazomib, carfilzomib (Kyprolis); Glutaminase inhibitors such as CB-839; vaccines such as peptide vaccine TG-01 (RAS), bacterial vector vaccines such as CRS-207/GVAX, autologous Gp96 vaccine, dendritic cells vaccines, Oncoquest-L vaccine, DPX-Survivac, ProstAtak, DCVAC, ADXS31-142, demcizumab (anti-DLL4, Delta-like ligand 4, Notch pathway), napabucasin (BBI-608) smoothened (SMO) receptor inhibitors, such as Odomzo® (sonidegib, formerly LDE-225), LEQ506, vismodegib (GDC-0449), BMS-833923, glasdegib (PF-04449913), LY2940680, and itraconazole; interferon alpha ligand modulators, such as interferon alfa-2b, interferon alpha-2a biosimilar (Biogenomics), ropeginterferon alfa-2b (AOP-2014, P-1101, PEG IFN alpha-2b), Multiferon (Alfanative, Viragen), interferon alpha 1b, Roferon-A (Canferon, Ro-25-3036), interferon alfa-2a follow-on biologic (Biosidus) (Inmutag, Inter 2A), interferon alfa-2b follow-on biologic (Biosidus-Bioferon, Citopheron, Ganapar) (Beijing Kawin Technology-Kaferon) (AXXO-interferon alfa-2b), Alfaferone, pegylated interferon alpha-1b, peginterferon alfa-2b follow-on biologic (Amega), recombinant human interferon alpha-1b, recombinant human interferon alpha-2a, recombinant human interferon alpha-2b, veltuzumab-IFN alpha 2b conjugate, Dynavax (SD-101), and interferon alfa-n1 (Humoferon, SM-10500, Sumiferon); interferon gamma ligand modulators, such as interferon gamma (OH-6000, Ogamma 100); IL-6 receptor modulators, such as tocilizumab, siltuximab, AS-101 (CB-06-02, IVX-Q-101); Telomerase modulators, such as tertomotide (GV-1001, HR-2802, Riavax) and imetelstat (GRN-163, JNJ-63935937) DNA methyltransferases inhibitors, such as temozolomide (CCRG-81045), decitabine, guadecitabine (S-110, SGI-110), KRX-0402, and azacitidine; DNA gyrase inhibitors, such as pixantrone and sobuzoxane; Bcl-2 family protein inhibitor ABT-263, venetoclax (ABT-199), ABT-737, and AT-101; Notch inhibitors such as LY3039478, tarextumab (anti-Notch2/3), BMS-906024 anti-myostatin inhibitors such as landogrozumab, hyaluronidase stimulators such as PEGPH-20, Wnt pathway inhibitors such as SM-04755, PRI-724, gamma-secretase inhibitors such as PF-03084014, IDO inhibitors such as indoximod, Grb-2 (growth factor receptor bound protein-2)

inhibitor BP1001 (liposomal Grb-2), TRAIL pathway-inducing compounds, such as ONC201, Focal adhesion kinase inhibitors such as VS-4718, defactinib, hedgehog inhibitors such as saridegib, sonidegib (LDE225), glasdegib and vismodegib, Aurora kinase inhibitors such as alisertib (MLN-8237), modulators of HSPB1 activity (heat shock protein 27, HSP27), such as brivudine, apatorsen, ATR inhibitor such as AZD6738, and VX-970, mTOR inhibitors, such as sapanisertib, Hsp90 inhibitors such as AUY922. Murine double minute (mdm2) oncogene inhibitors such as DS-3032b CD137 agonist such as urelumab, Anti-KIR monoclonal antibodies such as lirilumab (IPH-2102). Antigen CD19 inhibitors such as MOR208, MEDI-551, AFM-11, CD44 binders such as A6, CYP17 inhibitors, such as VT-464, ASN-001, ODM-204. RXR agonists such as IRX4204, TLRs (Toll-like receptors) agonists such as IMO-8400 A hedgehog/smoothened (hh/Smo) antagonist such as taladegib. Immunomodulators such as complement C3 modulators, such as Imprime PGG. Intratumoral immune-oncology agents such as G100 (TLR4 agonist) IL-15 agonists such as ALT-803 EZH2 (enhancer of zeste homolog 2) inhibitors such as tazemetostat. Oncolytic viruses, such as pelareorep, and talimogene laherparepvec). DOT1L (histone methyltransferase) inhibitors such as pinometostat (EPZ-5676), toxins such as Cholera toxin, ricin, *Pseudomonas* exotoxin, *Bordetella pertussis* adenylate cyclase toxin, diphtheria toxin, and caspase activators; and chromatin. DNA plasmid such as BC-819. PLK inhibitors of PLK 1, 2, and 3, such as volasertib (PLK1). Apoptosis Signal-Regulating Kinase (ASK) Inhibitors: ASK inhibitors include ASK1 inhibitors. Examples of ASK1 inhibitors include, but are not limited to, those described in WO 2011/008709 (Gilead Sciences) and WO 2013/112741 (Gilead Sciences). Bruton's Tyrosine Kinase (BTK) Inhibitors: Examples of BTK inhibitors include, but are not limited to, (S)-6-amino-9-(1-(but-2-ynoyl)pyrrolidin-3-yl)-'7-(4-phenoxyphenyl)-7H-pur-in-8 (9H)-one, acalabrutinib (ACP-196), BGB-3111, HM71224, ibrutinib, M-2951, ONO-4059, PRN-1008, spebrutinib (CC-292), TAK-020. Cyclin-dependent Kinase (CDK) Inhibitors: CDK inhibitors include inhibitors of CDK 1, 2, 3, 4, 6 and 9, such as abemaciclib, alvocidib (HMR-1275, flavopiridol), AT-7519, FLX-925, LEE001, palbociclib, ribociclib, rigosertib, selinexor, UCN-01, and TG-02. Discoidin Domain Receptor (DDR) Inhibitors: DDR inhibitors include inhibitors of DDR1 and/or DDR2. Examples of DDR inhibitors include, but are not limited to, those disclosed in WO 2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO 2013/034933 (Imperial Innovations). Histone Deacetylase (HDAC) Inhibitors: Examples of HDAC inhibitors include, but are not limited to, abexinostat, ACY-241, AR-42, BEBT-908, belinostat, CKD-581, CS-055 (HBI-8000), CUDC-907, entinostat, givinostat, mocetinostat, panobinostat, pracinostat, quisinostat (JNJ-26481585), resminostat, ricolinostat, SHP-141, valproic acid (VAL-001), vorinostat. Janus Kinase (JAK) Inhibitors: JAK inhibitors inhibit JAK1, JAK2, and/or JAK3. Examples of JAK inhibitors include, but are not limited to, AT9283, AZD1480, baricitinib, BMS-911543, fedratinib, filgotinib (GLPG0634), gandotinib (LY2784544), INCB039110, lestaurtinib, momelotinib (CYT0387), NS-018, pacritinib (SB1518), peficitinib (ASP015K), ruxolitinib, tofacitinib (formerly tasocitinib), and XL019. Lysyl Oxidase-Like Protein (LOXL) Inhibitors: LOXL inhibitors include inhibitors of LOXL1, LOXL2, LOXL3, LOXL4, and/or LOXL5. Examples of LOXL inhibitors include, but are not limited to, the antibodies described in WO 2009/017833 (Arresto Biosciences). Examples of LOXL2 inhibitors include, but are not limited to, the antibodies described in WO 2009/017833 (Arresto Biosciences), WO 2009/035791 (Arresto Biosciences), and WO 2011/097513 (Gilead Biologics). Matrix Metalloprotease (MMP) Inhibitors: MMP inhibitors include inhibitors of MMP1 through 10. Examples of MMP9 inhibitors include, but are not limited to, marimastat (BB-2516), cipemastat (Ro 32-3555) and those described in WO 2012/027721 (Gilead Biologics). Mitogen-activated Protein Kinase (MEK) Inhibitors: MEK inhibitors include antroquinonol, binimetinib, cobimetinib (GDC-0973, XL-518), MT-144, selumetinib (AZD6244), sorafenib, trametinib (GSK1120212), uprosertib+trametinib. Phosphatidylinositol 3-kinase (PI3K) Inhibitors: PI3K inhibitors include inhibitors of PI3K.gamma., PI3K.delta., PI3.beta., PI3K.alpha., and/or pan-PI3K. Examples of PI3K inhibitors include, but are not limited to, ACP-319, AEZA-129, AMG-319, AS252424, BAY 10824391, BEZ235, buparlisib (BKM120), BYL719 (alpelisib), CH5132799, copanlisib (BAY 80-6946), duvelisib, GDC-0941, GDC-0980, GSK2636771, GSK2269557, idelalisib (Zydelig®), IPI-145, IPI-443, KAR4141, LY294002, Ly-3023414, MLN1117, OXY111A, PA799, PX-866, RG7604, rigosertib, RP5090, taselisib, TG100115, TGR-1202, TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences). Spleen Tyrosine Kinase (SYK) Inhibitors: Examples of SYK inhibitors include, but are not limited to, 6-(1H-indazol-6-yl)-N-(4-morpholinophenyl)imidazo[1,2-alpyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Conn.). and those described in U.S. 2015/0175616. Tyrosine-kinase Inhibitors (TKIs): TKIs may target epidermal growth factor receptors (EGFRs) and receptors for fibroblast growth factor (FGF), platelet-derived growth factor (PDGF), and vascular endothelial growth factor (VEGF). Examples of TKIs include, but are not limited to, afatinib, bosutinib, brigatinib, cabozantinib, crenolanib, dacomitinib, dasatinib, dovitinib, E-6201, erlotinib, gefitinib, gilteritinib (ASP-2215), HM61713, icotinib, imatinib, KX2-391 (Src), lapatinib, lestaurtinib, midostaurin, nintedanib, osimertinib (AZD-9291), ponatinib, poziotinib, quizartinib, radotinib, rociletinib, sunitinib, and TH-4000. Further anticancer agents include: alkylating agents such as thiotepa and cyclophosphamide (CYTOXAN); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, especially bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlomaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromophores, aclacinomycins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenishers such as frolinic acid; radiotherapeutic agents such as Radium-223; trichothecenes, especially T-2 toxin, verracurin A, roridin A, and anguidine; taxoids such as paclitaxel) (TAXOL), abraxane, docetaxel) (TAXOTERE), cabazitaxel, BIND-014; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformithine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2''-tricUorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine) (GEMZAR™); 6-thioguanine; mercaptopurine; methotrexate; vinblastine; platinum; etoposide (VP-16); ifosfamide; mitroxantrone; vancristine; vinorelbine) (NAVELBINE™); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; FOLFIRI (fluorouracil, leucovorin, and irinotecan); and pharmaceutically acceptable salts, acids, or derivatives of any of the above.

Also included in the definition of anticancer agents are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors. Examples of anti-estrogens and SERMs include, for example, tamoxifen (including NOLVADEX), raloxifene, droloxifene, 4-hydroxytamoxifen, trioxifene, keoxifene, LY117018, onapristone, and toremifene) (FARESTON). Inhibitors of the enzyme aromatase regulate estrogen production in the adrenal glands. Examples include 4(5)-imidazoles, aminoglutethimide, megestrol acetate) (MEGACE), exemestane, formestane, fadrozole, vorozole) (RIVISOR), letrozole) (FEMARA), and anastrozole) (ARIMIDEX). Examples of anti-androgens include apalutamide, abiraterone, enzalutamide, flutamide, galeterone, nilutamide, bicalutamide, leuprolide, goserelin, ODM-201, APC-100, ODM-204. Examples of progesterone receptor antagonist include onapristone.

Anti-angiogenic agents include, but are not limited to, retinoid acid and derivatives thereof, 2-methoxyestradiol, ANGIOSTATIN, ENDOSTATIN, regorafenib, necuparanib, suramin, squalamine, tissue inhibitor of metalloproteinase-1, tissue inhibitor of metalloproteinase-2, plasminogen activator inhibitor-1, plasminogen activator inbibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cis-hydroxyproline, d,l-3,4-dehydroproline, thiaproline, .alpha., .alpha.'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-fibrotic agents include, but are not limited to, the compounds such as beta-aminopropionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethy)dithio)butanoic acid, p-2-amino-3-methyl-3-((2-aminoethy)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

The immunotherapeutic agents include and are not limited to therapeutic antibodies suitable for treating patients. Some examples of therapeutic antibodies include simtuzumab, abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, dinutuximab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, pasudotox, narnatumab, naptumomab, necitumumab, nimotuzumab, nofetumomab, obinutuzumab, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, tacatuzumab, taplitumomab, tenatumomab, teprotumumab, tigatuzumab, tositumomab, trastuzumab, ABP-980, tucotuzumab, ubilituximab, veltuzumab, vorsetuzumab, votumumab, zalutumumab, CC49, OBI-833 and 3F8. Rituximab can be used for treating indolent B-cell cancers, including marginal-zone lymphoma, WM, CLL and small lymphocytic lymphoma. A combination of Rituximab and chemotherapy agents is especially effective.

The exemplified therapeutic antibodies may be further labeled or combined with a radioisotope particle such as indium-111, yttrium-90 (90Y-clivatuzumab), or iodine-131.

10. Exemplary Uses

The methods of the invention can be used to produce nanoparticles and microparticles that have numerous applications.

Preferably, the nanoparticles and microparticles can be used in a method of treating a disease or condition in a subject in need thereof, or a method of reducing the duration or severity of the disease or condition in the subject in need thereof, wherein the disease or condition is treatable with microparticles or nanoparticles with negative surface charge (and optionally with a specific API), comprising administering a composition or a pharmaceutical composition comprising the microparticles or nanoparticles to the subject, thereby treating the disease or condition.

In a related aspect, the invention provides a method of regulating an immune response in a subject in need thereof, preferably a mammal, more preferably a human, comprising administering a composition or a pharmaceutical composition comprising the microparticles or nanoparticles to the subject, thereby regulating the immune response. Methods of immunoregulation provided by the invention include those that suppress and/or inhibit an innate immune response or an adaptive immune response, including, but not limited to, an immune response stimulated by immunostimulatory polypeptides or viral or bacterial components. The subject particles are administered in an amount sufficient to regulate the immune response. As described herein, regulation of an immune response may be humoral and/or cellular, and is measured using standard techniques in the art and as described herein.

Preferably, the disease or condition can be characterized by an inflammatory immune response.

Treatable diseases or conditions include, but are not limited to: an autoimmune disorder, such as multiple sclerosis, scleroderma, type-I diabetes, rheumatoid arthritis, thyroiditis, systemic lupus erythmatosis, Reynauud's syndrome, Sjorgen's syndrome, autoimmune uveitis, autoimmune myocarditis, or Crohn's disease. Preferably, the autoimmune disease is multiple sclerosis. An individual having an autoimmune disease or inflammatory disease is an individual with a recognizable symptom of an existing autoimmune disease or inflammatory disease.

Autoimmune diseases can be divided in two broad categories: organ-specific and systemic. Autoimmune diseases include, without limitation, rheumatoid arthritis (RA), systemic lupus erythematosus (SLE), type I diabetes mellitus, type II diabetes mellitus, multiple sclerosis (MS), immune-mediated infertility such as premature ovarian failure, scleroderma, Sjogren's disease, vitiligo, alopecia (baldness), polyglandular failure, Grave's disease, hypothyroidism, polymyositis, *Pemphigus vulgaris, Pemphigus foliaceus*, inflammatory bowel disease including Crohn's disease and ulcerative colitis, autoimmune hepatitis including that associated with hepatitis B virus (HBV) and hepatitis C virus (HCV), hypopituitarism, graft-versus-host disease (GvHD), myocarditis, Addison's disease, autoimmune skin diseases, uveitis, pernicious anemia, and hypoparathyroidism.

Autoimmune diseases may also include, without limitation, Hashimoto's thyroiditis, Type I and Type II autoimmune polyglandular syndromes, paraneoplastic pemphigus, bullus pemphigoid, dermatitis herpetiformis, linear IgA disease, epidermolysis bullosa acquisita, erythema nodosa, pemphigoid gestationis, cicatricial pemphigoid, mixed essential cryoglobulinemia, chronic bullous disease of childhood, hemolytic anemia, thrombocytopenic purpura, Goodpasture's syndrome, autoimmune neutropenia, myasthenia gravis, Eaton-Lambert myasthenic syndrome, stiff-man syndrome, acute disseminated encephalomyelitis, Guillain-Barré syndrome, chronic inflammatory demyelinating polyradiculoneuropathy, multifocal motor neuropathy with conduction block, chronic neuropathy with monoclonal gammopathy, opsoclonus-myoclonus syndrome, cerebellar degeneration, encephalomyelitis, retinopathy, primary biliary sclerosis, sclerosing cholangitis, gluten-sensitive enteropathy, ankylosing spondylitis, reactive arthritides, polymyositis/dermatomyositis, mixed connective tissue disease, Behcet's syndrome, psoriasis, polyarteritis nodosa, allergic anguitis and granulomatosis (Churg-Strauss disease), polyangiitis overlap syndrome, hypersensitivity vasculitis, Wegener's granulomatosis, temporal arteritis, Takayasu's arteritis, Kawasaki's disease, isolated vasculitis of the central nervous system, thromboangiitis obliterans, sarcoidosis, glomerulonephritis, and cryopathies. These conditions are well known in the medical arts and are described, for example, in *Harrison's Principles of Internal Medicine,* 14th edition, Fauci, A. S. et al., Eds., New York: McGraw-Hill, 1998.

Preferably, the diseases or conditions include an allergic disorder or condition, such as allergic disease, allergy, eczema, asthma, allergic rhinitis or skin hypersensitivity. An individual having an allergic disease or asthma is an individual with a recognizable symptom of an existing allergic disease or asthma.

Preferably, the diseases or conditions include bacterial or viral infection. An individual having a bacterial or viral infection is an individual with a recognizable symptom of an existing bacterial or viral infection.

Preferably, the subject has a viral infection. Preferably, the viral infection is a herpes virus infection, a hepatitis virus infection, a West Nile virus infection, a flavivirus, an influenza infection, a rhinovirus infection, a papillomavirus infection, a paramyxovirus infection, or a parainfluenza virus infection. Preferably, the viral infection infects the central nervous system of said subject. Preferably, the viral infection causes viral encephalitis or viral meningitis.

Preferably, the subject has a bacterial infection. A non-limiting list of bacterial infections treatable with the subject particles of the current invention include *Staphylococcus* infections, *Streptococcus* infections, mycobacterial infections, *Bacillus* infections, *Salmonella* infections, *Vibrio* infections, spirochete infections, and *Neisseria* infections. Preferred are bacteria that infect the central nervous system of the subject. Most preferred are bacteria that cause encephalitis or meningitis.

Preferably, the method of the invention induces immune tolerance when administered to a subject with a bacterial or viral infection. Preferably, the method ameliorates or dampens an inflammatory immune response when administered to a subject with a bacterial or viral infection.

Preferably, the subject is a transplant recipient. Transplantation refers to the transfer of a tissue sample or graft from a donor individual to a recipient individual and is frequently performed on human recipients who need the tissue in order to restore a physiological function provided by the tissue. Tissues that are transplanted include (but are not limited to) whole organs such as kidney, liver, heart, lung; organ components such as skin grafts and the cornea of the eye; and cell suspensions such as bone marrow cells and cultures of cells selected and expanded from bone marrow or circulating blood, and whole blood transfusions.

A serious potential complication of any transplantation ensues from antigenic differences between the host recipient and the engrafted tissue. Depending on the nature and degree of the difference, there may be a risk of an immunological assault of the graft by the host, or of the host by the graft, or both, may occur. The extent of the risk is determined by following the response pattern in a population of similarly treated subjects with a similar phenotype and correlating the various possible contributing factors according to well accepted clinical procedures. The immunological assault may be the result of a preexisting immunological response (such as preformed antibody), or one that is initiated about the time of transplantation (such as the generation of TH cells). Antibody, T helper (TH) cells, or cytotoxic T (Tc) cells may be involved in any combination with each other and with various effector molecules and cells. However, the antigens which are involved in the immune response are generally not known, therefore posing difficulties in designing antigen-specific therapies or inducing antigen-specific tolerance. The modified particles of the current invention are particularly useful in preventing the rejection of organs because no attached peptides or antigens need to be conjugated to the modified particles in order for the particles to be effective in inducing tolerance or ameliorate an inflammatory immune response.

Preferably the invention relates to decreasing the risk of host versus graft disease, leading to rejection of the tissue graft by the recipient. The treatment may be performed to prevent or reduce the effect of a hyperacute, acute, or chronic rejection response. Treatment is preferentially initiated sufficiently far in advance of the transplant so that tolerance will be in place when the graft is installed; but where this is not possible, treatment can be initiated simultaneously with or following the transplant. Regardless of the time of initiation, treatment will generally continue at regular intervals for at least the first month following transplant. Follow-up doses may not be required if a sufficient accommodation of the graft occurs, but can be resumed if there is any evidence of rejection or inflammation of the graft. Of course, the tolerization procedures of this invention may be combined with other forms of immunosuppression to achieve an even lower level of risk.

Preferably, the diseases or conditions include unwanted immune activation, such as atherosclerosis, ischemic reperfusion injury, and myocardial infarction.

Preferably, the invention relates to treatment of pathological conditions pertaining to an unwanted hypersensitivity. The hypersensitivity can be any one of types I, II, III, and IV, Immediate (type I) hypersensitivity. The frequency of administration will typically correspond with the timing of allergen exposure. Suitable animal models are known in the art (for example, Gundel et al., *Am. Rev. Respir. Dis.,* 146:369, 1992, Wada et al, *J. Med. Chem.,* 39:2055, 1996; and WO 96/35418).

Preferably, treatable diseases or conditions include those initiated by inflammatory monocytes, autoimmunity, cardiovascular disease (such as cardiac ischemia, or ischemia-reperfusion injury following cardiac infarction and transplantation), viral encephalitis, multiple sclerosis (MS), inflammatory bowel disease (IBD), peritonitis, lethal flavivirus encephalitis, immunopathological viral infections (including Influenza and West Nile Virus (WNV)), rheumatoid arthritis, HIV encephalitis, chronic liver disease, atherosclerosis, cardiac infarction, experimental autoimmune encephalomyelitis (EAE) and its corresponding diseases, Colitis, ulcerative colitis, etc.

A preferred condition for use in the claimed invention is treating cancers. Patients and cancers treated herein include Burkitt's lymphoma, Hodgkin's lymphoma, non-Hodgkin's lymphoma (NHL), indolent non-Hodgkin's lymphoma (iNHL), refractory iNHL, multiple myeloma (MM), chronic myeloid leukemia (CIVIL), acute lymphocytic leukemia (ALL), B-cell ALL, acute myeloid leukemia (AML), chronic lymphocytic leukemia (CLL), small lymphocytic lymphoma (SLL), myelodysplastic syndrome (MDS), myeloproliferative disease (MPD), mantle cell lymphoma (MCL), follicular lymphoma (FL), Waldestrom's macroglobulinemia (WM), T-cell lymphoma, B-cell lymphoma, diffuse large B-cell lymphoma (DLBCL), or marginal zone lymphoma (MZL). In one embodiment, the cancer is minimal residual disease (MRD). In additional embodiment, the cancer is selected from Hodgkin's lymphoma, non-Hodgkin's lymphoma (NHL), indolent non-Hodgkin's lymphoma (iNHL), and refractory iNHL. In certain embodiment, the cancer is indolent non-Hodgkin's lymphoma (iNHL). In some embodiment, the cancer is refractory iNHL. In one embodiment, the cancer is chronic lymphocytic leukemia (CLL). In other embodiment, the cancer is diffuse large B-cell lymphoma (DLBCL).

In certain embodiments, the cancer is a solid tumor and is selected from the group consisting of pancreatic cancer; bladder cancer; colorectal cancer; breast cancer, including metastatic breast cancer; prostate cancer, including androgen-dependent and androgen-independent prostate cancer; kidney or renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma, hepatic carcinoma, rectal cancer, penile carcinoma, vulval cancer, thyroid cancer, salivary gland carcinoma, endometrial or uterine carcinoma, hepatoma, hepatocellular cancer, liver cancer, gastric or stomach cancer including gastrointestinal cancer, cancer of the peritoneum, squamous carcinoma of the lung, gastroesophageal cancer, biliary tract cancer, gall bladder cancer, colorectal/appendiceal cancer, squamous cell cancer (e.g., epithelial squamous cell cancer).

Any of the methods of treatment provided may be used to treat cancer at various stages. By way of example, the cancer stage includes but is not limited to early, advanced, locally advanced, remission, refractory, reoccurred after remission and progressive.

Preferably, the microparticle or nanoparticle of the invention (e.g., those produced with the methods of the invention) can be used in combination with a second therapeutic that is effective for treating any one of the treatable conditions.

Preferably, the subject is a human patient. Preferably, the subject is a non-human mammal, such as a non-human primate, a livestock animal (horse, mule, cattle, bull, cow, sheep, goat, pig, camel, etc.), a rodent (rabbit, hamster, mouse, rat, etc.), or a pet (cat, dog).

Preferably, the method includes administering the subject composition or pharmaceutical composition comprising the subject microparticles or nanoparticles (e.g., the sulfated particles) by any suitable means or routes, such as orally, nasally, intravenously, intramuscularly, ocularly, transdermally, subcutaneously, intratumorally, intravesicularly, intra-articularly, intracranially, and intraperitoneally.

Preferably, about $10^2$ to about $10^{20}$ particles are provided to the individual. Preferably, between about $10^3$ to about $10^{15}$ particles are provided. Preferably, between about $10^6$ to about $10^{12}$ particles are provided. Preferably, between about $10^8$ to about $10^{10}$ particles are provided. Preferably, the preferred dose is 0.1% solids/ml. Therefore, for 0.5 μm beads, a preferred dose is approximately $4\times10^9$ beads, for 0.05 μm beads, a preferred dose is approximately $4\times10^{12}$ beads, for 3 μm beads, a preferred dose is $2\times10^7$ beads. However, a dose that is effective in treating the particular condition to be treated is encompassed by the current invention.

Preferably, the subject composition or subject pharmaceutical composition containing the subject microparticles or nanoparticles (e.g., sulfated particles) induces immune tolerance when administered to the subject in need thereof.

Preferably, the subject composition or subject pharmaceutical composition containing the subject microparticles or nanoparticles (e.g., sulfated particles) ameliorates an inflammatory immune response when administered to the subject in need thereof.

11. Efficacy Tests

The effectiveness of the subject microparticles and nanoparticles against the treatable diseases and conditions can be tested using a number of efficacy tests, including suitable animal models.

A proxy for tolerogenic activity is the ability of a particle to stimulate the production of an appropriate cytokine at the target site. The immunoregulatory cytokine released by T suppressor cells at the target site is thought to be TGF-β (Miller et al., *Proc. Natl. Acad. Sci. USA*, 89:421, 1992). Other factors that may be produced during tolerance are the cytokines IL-4 and IL-10, and the mediator PGE. In contrast, lymphocytes in tissues undergoing active immune destruction secrete cytokines such as IL-1, IL-2, IL-6, and IFNγ. Hence, the efficacy of a subject particle can be evaluated by measuring its ability to stimulate the appropriate type of cytokines.

For example, a rapid screening test for a subject particle, effective mucosal binding components, effective combinations, or effective modes and schedules of mucosal administration can be conducted using animal model systems. Animals are treated at a mucosal surface with the test particle composition, and at some time are challenged with administration of the disease causing antigen or an infectious agent. Spleen cells are isolated and cultured in vitro in the presence of the disease causing antigen or an antigen derived from the infectious agent at a concentration of about 50 μg/mL. Cytokine secretion into the medium can be quantified by standard immunoassay.

The ability of the subject particles to suppress the activity of cells can be determined using cells isolated from an animal immunized with the modified particles, or by creating a cell line responsive to a disease causing antigen or viral antigen target antigen (Ben-Nun et al., *Eur. J. Immunol.*, 11195, 1981). In one variation of this experiment, the suppressor cell population is mildly irradiated (about 1000 to 1250 rads) to prevent proliferation, the suppressors are co-cultured with the responder cells, and then tritiated thymidine incorporation (or MTT) is used to quantitate the proliferative activity of the responders. In another variation, the suppressor cell population and the responder cell population are cultured in the upper and lower levels of a dual chamber transwell culture system (Costar, Cambridge Mass.), which permits the populations to co-incubate within 1 mm of each other, separated by a polycarbonate membrane (WO 93/16724). In this approach, irradiation of the suppressor cell population is unnecessary, since the proliferative activity of the responders can be measured separately.

The effectiveness of compositions and modes of administration for treatment of specific disease can also be elaborated in a corresponding animal disease model. The ability of the treatment to diminish or delay the symptomatology of the disease is monitored at the level of circulating biochemical and immunological hallmarks of the disease, immunohistology of the affected tissue, and gross clinical features as appropriate for the model being employed. Non-limiting examples of animal models that can be used for testing are included below.

For example, animal models for the study of autoimmune disease are known in the art. Animal models which appear most similar to human autoimmune disease include animal strains which spontaneously develop a high incidence of the particular disease. Examples of such models include, but are not limited to, the non-obese diabetic (NOD) mouse, which develops a disease similar to type 1 diabetes, and lupus-like disease prone animals, such as New Zealand hybrid, MRL-Faslpr and BXSB mice. Animal models in which an autoimmune disease has been induced include, but are not limited to, experimental autoimmune encephalomyelitis (EAE), which is a model for multiple sclerosis, collagen-induced arthritis (CIA), which is a model for rheumatoid arthritis, and experimental autoimmune uveitis (EAU), which is a model for uveitis. Animal models for autoimmune disease have also been created by genetic manipulation and include, for example, IL-2/IL-10 knockout mice for inflammatory bowel disease, Fas or Fas ligand knockout for SLE, and IL-1 receptor antagonist knockout for rheumatoid arthritis.

The invention contemplates modulation of tolerance by modulating TH1 response, TH2 response, TH17 response, or a combination of these responses. Modulating TH1 response encompasses changing expression of, e.g., interferon-gamma. Modulating TH2 response encompasses changing expression of, e.g., any combination of IL-4, IL-5, IL-10, and IL-13. Typically, an increase (decrease) in TH2 response will comprise an increase (decrease) in expression of at least one of IL-4, IL-5, IL-10, or IL-13; more typically an increase (decrease) in TH2 response will comprise an increase in expression of at least two of IL-4, IL-5, IL-10, or IL-13, most typically an increase (decrease) in TH2 response will comprise an increase in at least three of IL-4, IL-5, IL-10, or IL-13, while ideally an increase (decrease) in TH2 response will comprise an increase (decrease) in expression of all of IL-4, IL-5, IL-10, and IL-13. Modulating TH17 encompasses changing expression of, e.g., TGF-beta, IL-6, IL-21 and IL-23, and effects levels of IL-17, IL-21 and IL-22.

Tolerance to autoantigens and autoimmune disease is achieved by a variety of mechanisms including negative selection of self-reactive T cells in the thymus and mechanisms of peripheral tolerance for those autoreactive T cells that escape thymic deletion and are found in the periphery. Examples of mechanisms that provide peripheral T cell tolerance include "ignorance" of self-antigens, anergy or unresponsiveness to autoantigen, cytokine immune deviation, and activation-induced cell death of self-reactive T cells. In addition, regulatory T cells have been shown to be involved in mediating peripheral tolerance. See, for example, Walker et al. (2002) *Nat. Rev. Immunol.*, 2:11-19; Shevach et al. (2001) *Immunol. Rev.*, 182:58-67. In some situations, peripheral tolerance to an autoantigen is lost (or broken) and an autoimmune response ensues. For example, in an animal model for EAE, activation of antigen presenting cells (APCs) through TLR innate immune receptors was shown to break self-tolerance and result in the induction of EAE (Waldner et al. (2004) *J. Clin. Invest.*, 113:990-997).

Preferably, the invention provides methods for increasing antigen presentation while suppressing or reducing TLR7/8, TLR9, and/or TLR 7/8/9 dependent cell stimulation. As described herein, administration of particular subject particles results in antigen presentation by DCs or APCs while suppressing the TLR 7/8, TLR9, and/or TLR7/8/9 dependent cell responses associated with immunostimulatory polynucleotides. Such suppression may include decreased levels of one or more TLR-associated cytokines.

The subject invention also provides novel compounds that have biological properties useful for the treatment of Mac-1 and LFA-1 mediated disorders.

12. Pharmaceutical Composition

One aspect of the present invention provides pharmaceutical compositions which comprise the subject microparticles and nanoparticles, and optionally comprise a pharmaceutically acceptable carrier. Preferably, these compositions optionally further comprise one or more additional therapeutic agents. Alternatively, the subject particles of the current invention may be administered to a patient in need thereof in combination with the administration of one or more other therapeutic agents. For example, additional therapeutic agents for conjoint administration or inclusion in a pharmaceutical composition with a compound of this invention may be an approved anti-inflammatory agent, or it may be any one of a number of agents undergoing approval in the Food and Drug Administration that ultimately obtain approval for the treatment of any disorder characterized by an uncontrolled inflammatory immune response or a bacterial or viral infection. It will also be appreciated that certain of the subject particles of present invention can exist in free form for treatment, or where appropriate, as a pharmaceutically acceptable derivative thereof.

Preferably, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention.

Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S. P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility.

Solid dosage forms for oral administration include capsules, tablets, pills, powders, and granules. In such solid dosage forms, the modified particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The microparticles and nanoparticles can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the modified particles only, or preferentially, in a certain part of the intestinal tract, optionally, in a delayed manner. Examples of embedding compositions which can be used include polymeric substances and waxes.

The present invention encompasses pharmaceutically acceptable topical formulations of the sulfated microparticles and nanoparticles. The term "pharmaceutically acceptable topical formulation," as used herein, means any formulation which is pharmaceutically acceptable for intradermal administration of the subject microparticles/nanoparticles by application of the formulation to the epidermis. Preferably of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, *Remington's Pharmaceutical Sciences*, 16th Edition, 1980 and 17th Edition, 1985, both published by Mack Publishing Company, Easton, Pa., the disclosures of which are incorporated herein by reference in their entireties. Preferably, the topical formulations of the invention may comprise excipients. Any pharmaceutically acceptable excipient known in the art may be used to prepare the inventive pharmaceutically acceptable topical formulations.

Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the modified particles. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

Preferably, the pharmaceutically acceptable topical formulations of the invention comprise at least the sulfated microparticles and nanoparticles and a penetration enhancing agent. The choice of topical formulation will depend or several factors, including the condition to be treated, the physicochemical characteristics of the particles and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, 111 (1997). Preferably, penetration agents for use with the invention include, but are not limited to, triglycerides (e.g., soybean oil), aloe compositions (e.g., aloe vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methylpyrrolidone.

Preferably, the compositions may be in the form of ointments, pastes, creams, lotions, gels, powders, solutions, sprays, inhalants or patches. Preferably, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy stearate. Preferably, the active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

The sulfated microparticles and nanoparticles can be administered by aerosol. This is accomplished by preparing an aqueous aerosol, liposomal preparation or solid particles containing the modified particles. A non-aqueous (e.g., fluorocarbon propellant) suspension could be used. Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

It will also be appreciated that the sulfated nanoparticles and microparticles and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-inflammatory agent), or they may achieve different effects (e.g., control of any adverse effects).

Preferably, the pharmaceutical compositions containing the sulfated particles of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, anti-nausea medications and anti-sickness drugs.

The following examples are given to illustrate the present invention. It should be understood, however, that the invention is not to be limited to the specific conditions or details described in these examples. Throughout the specification, any and all references to a publicly available document, including any U.S. patent or patent application publication, are specifically incorporated by reference.

EXAMPLES

Example 1. Preparation of PLGA Nanoparticles Having Heparan Sulfate on the Surface 200 mg PLGA (LACTEL Absorbable Polymers B6013-2P) is dissolved in 8 ml ethyl acetate. The PLGA solution is mixed with 40 mL 0.5% polyvinyl alcohol (89%) solution containing 40 mg (1 mg/mL) of heparan sulfate, and homogenized at 18,000 rpm for 1 minute using an IKA® DIGITAL ULTRA-TURRAX® T25 Homogenizer. The resulting emulsion is poured into a glass container and stirred magnetically at 400 rpm for 3-5 hours to allow the evaporation of the solvent. The nanoparticles are then washed two times with distilled water by centrifugation. The purified particles are found to have an average particle size of 550 nm, and a zeta potential of −35 mV.

Example 2. Preparation of PLGA Nanoparticles Having Carrageenan on the Surface 200 mg PLGA (LACTEL Absorbable Polymers B6013-2P) is dissolved in 8 ml ethyl acetate. The PLGA solution is mixed with 40 mL 0.5% polyvinyl alcohol (89%) solution containing 40 mg (1 mg/mL) of carrageenan, and homogenized at 18,000 rpm for 1 minute using an IKA® DIGITAL ULTRA-TURRAX® T25 Homogenizer. The resulting emulsion is poured into a glass container and stirred magnetically at 400 rpm for 3-5 hours to allow the evaporation of the solvent. The nanoparticles are then washed two times with distilled water by centrifugation. The purified particles are found to have an average particle size of 550 nm, and a zeta potential of −36 mV.

Example 3. Preparation of PLGA Nanoparticles Having Ulvan on the Surface 200 mg PLGA (LACTEL Absorbable Polymers B6013-2P) is dissolved in 8 ml ethyl acetate. The PLGA solution is mixed with 40 mL 0.5% polyvinyl alcohol (89%) solution containing 40 mg (1 mg/mL) of Ulvan, and homogenized at 18,000 rpm for 1 minute using an IKA® DIGITAL ULTRA-TURRAX® T25 Homogenizer. The resulting emulsion is poured into a glass container and stirred magnetically at 400 rpm for 3-5 hours to allow the evaporation of the solvent. The nanoparticles are then washed two times with distilled water by centrifugation. The purified particles are found to have an average particle size of 550 nm, and a zeta potential of −35 mV.

Example 4. Preparation of PLGA Nanoparticles Having Heparan Sulfate on the Surface 50 mg PLGA (LACTEL Absorbable Polymers B6010-2P) is dissolved in 2 ml ethyl acetate. The PLGA solution is mixed with 10 mL 0.1% Brij solution containing 100 mg (10 mg/mL) of heparan sulfate solution, and homogenized at 20,000 rpm for 1 minute using an IKA® DIGITAL ULTRA-TURRAX® T25 Homogenizer. The resulting emulsion is poured into a glass container and stirred magnetically at 400 rpm for 3-5 hours to allow the evaporation of the solvent. The nanoparticles are purified multiple times with distilled water by centrifugation. The nanoparticles are found to have an average particle size of 385.0 nm, and a zeta potential of −40.4 mV.

Example 5. Preparation of Highly Negatively Charged PLGA Nanoparticles Having Heparan Sulfate on the Surface and Loaded with Paclitaxel Via a Single Emulsification Process 0.9 g PLGA and 18 mg paclitaxel are dissolved in 18 mL ethyl acetate to form a PLGA-paclitaxel solution. The PLGA-paclitaxel solution is mixed with 80 mL 0.1% Brij solution containing 180 milligrams of heparan sulfate, and homogenized at 18,000 rpm for 1 minute using an IKA® DIGITAL ULTRA-TURRAX® T25 Homogenizer. The resulting emulsion is poured into a glass container and stirred magnetically at 400 rpm for 5 hours to allow the evaporation of the solvent. The paclitaxel loaded nanoparticles are then washed three times with distilled water before lyophilized. Particle size and zeta potential can be determined with a Malvern particle size analyzer (Worcestershire, UK).

Example 6. Preparation of Highly Negatively Charged PLGA Nanoparticles Having Fucoidan on the Surface and Loaded with Paclitaxel Via a Single Emulsification Process 0.9 g PLGA and 18 mg paclitaxel are dissolved in 18 mL ethyl acetate to form a PLGA-paclitaxel solution. The PLGA-paclitaxel solution is mixed with 80 mL 0.1% Brij solution containing 180 milligrams of fucoidan, and homogenized at 18,000 rpm for 1 minute using an IKA® DIGITAL ULTRA-TURRAX® T25 Homogenizer. The resulting emulsion is poured into a glass container and stirred magnetically at 400 rpm for 5 hours to allow the evaporation of the solvent. The paclitaxel loaded nanoparticles are then washed three times with distilled water before lyophilized. Particle size and zeta potential can be determined with a Malvern particle size analyzer (Worcestershire, UK).

Example 7. Preparation of BSA-Loaded, Highly Negatively Charged PLGA Nanoparticles Having Fucoidan on the Surface Via a Double Emulsification Process 0.9 g PLGA is dissolved in 18 mL ethyl acetate to form a PLGA solution. An aqueous solution consisting of 80 ml 0.1% Brij solution (in water), 6.5 ml of ethyl acetate, and 180 milligrams of fucoidan is prepared. 20 mg of bovine serum albumin (BSA, a model therapeutic protein) is dissolved in 2.0 mL of an aqueous buffer to form the protein solution. 1.8 mL of the BSA solution is mixed with the PLGA solution and homogenized using a homogenizer at 24,000 rpm for 45 seconds. The resulting emulsion is mixed with the Brij solution and homogenized at 18,000 rpm for 1 minute using another homogenizer. The resulting final emulsion is poured into a 1 L glass flask and the solvent is removed by rotor evaporation at a vacuum of 50 mbar. The BSA loaded particles are washed three times with distilled water before lyophilized. Particle size and zeta potential can be determined with a Malvern particle size analyzer (Worcestershire, UK).

Example 8. Wash Test 300 mg BSA loaded PLGA nanoparticles produced as described in Example 7 are reconstituted in 30 mL deionized water. After brief sonication, the particles are well suspended. A sample is taken for measurement of zeta potential. The zeta potential is found to be −42.7 mV. To such nanoparticle suspension is then added 300 mL of deionized water. The resulting mixture is concentrated using a tangential flow filtration (TFF) device to 30 mL and zeta potential is found to be −44.5 mV. This washing step is repeated two more times, and the resulting zeta potential is found to be −43.0 mV, and −40.1 mV, respectively, after each wash.

Example 9. Preparation of PLGA Nanoparticles Having Fucoidan on the Surface 0.2016 g PLGA (LACTEL Absorbable Polymers B6013-2P) was dissolved in 8 ml ethyl acetate. The PLGA solution was mixed with 40 mL 0.5% polyvinyl alcohol (89%) solution containing 40 mg (1 mg/mL) of fucoidan (from Fucus vesiculosus), and homogenized at 18,000 rpm for 1 minute using an IKA® DIGITAL ULTRA-TURRAX® T25 Homogenizer. The resulting emulsion was poured into a glass container and stirred magnetically at 400 rpm for 3-5 hours to allow the evaporation of the solvent. The nanoparticles were then washed two times with distilled water by centrifugation. The purified particles were found to have an average particle size of 546.5 nm, and a zeta potential of −28.5 mV.

Example 10. Preparation of PLGA Nanoparticles Having Fucoidan on the Surface 0.1990 g PLGA (LACTEL Absorbable Polymers B6010-2P) was dissolved in 8 ml ethyl acetate. The PLGA solution was mixed with 40 mL of 0.5% (5 mg/mL) fucoidan (from Fucus vesiculosus) solution, and homogenized at 24,000 rpm for 1 minute using an IKA® DIGITAL ULTRA-TURRAX® T25 Homogenizer. The resulting emulsion was poured into a glass container and stirred magnetically at 400 rpm for 3-5 hours to allow the evaporation of the solvent. The nanoparticles were purified multiple times with distilled water by centrifugation. The final particles were found to have an average particle size of 639.6 nm, and a zeta potential of −33.4 mV.

Example 11. Preparation of PLGA Nanoparticles Having Fucoidan on the Surface 50 mg PLGA (LACTEL Absorbable Polymers B6010-2P) was dissolved in 2 ml ethyl acetate. The PLGA solution was mixed with 10 mL 0.1% Brij solution containing 100 mg (10 mg/mL) of fucoidan (from Fucus vesiculosus) solution, and homogenized at 20,000 rpm for 1 minute using an IKA® DIGITAL ULTRA-TURRAX® T25 Homogenizer. The resulting emulsion was poured into a glass container and stirred magnetically at 400 rpm for 3-5 hours to allow the evaporation of the solvent. The nanoparticles were purified multiple times with distilled water by centrifugation. The nanoparticles were found to have an average particle size of 385.0 nm, and a zeta potential of −40.4 mV.

Example 12. Preparation of PLGA Nanoparticles Having Dextran Sulfate on the Surface 50 mg PLGA (LACTEL Absorbable Polymers B6010-2P) was dissolved in 2 ml ethyl acetate. The PLGA solution was mixed with 10 mL 0.1% Brij solution containing 100 mg (10 mg/mL) of dextran sulfate, and homogenized at 17,000 rpm for 1 minute using an IKA® DIGITAL ULTRA-TURRAX® T25 Homogenizer. The resulting emulsion was poured into a glass container and stirred magnetically at 400 rpm for 3-5 hours to allow the evaporation of the solvent. The nanoparticles were purified multiple times with distilled water by centrifugation. The nanoparticles were found to have an average particle size of 523.5 nm, and a zeta potential of −40.3 mV.

Example 13. Preparation of PLGA Nanoparticles Having Fucoidan on the Surface 25 mg PLGA (LACTEL Absorbable Polymers B6010-2P) was dissolved in 0.5 ml ethyl acetate. The PLGA solution was mixed with 2.5 mL 0.1% Brij solution containing 125 mg (50 mg/mL) of fucoidan (from Fucus vesiculosus) solution and sonicated at 50% for 45 seconds using Fisher Scientific CL-18. The resulting emulsion was poured into 20 mL 0.1% Brij solution to harden the nanoparticles quickly and continued stirring magnetically at 400 rpm for 3-5 hours to ensure the evaporation of the solvent. The nanoparticles were found to have an average particle size of 201.3 nm, and a zeta potential of −32.1 mV.

Example 14. Preparation of PLGA Nanoparticles Having Fucoidan on the Surface 52.5 mg PLGA (LACTEL Absorbable Polymers B6010-2P) was dissolved in 2 ml ethyl acetate. The PLGA solution was mixed with 10 mL 0.1% Brij solution containing 100 mg (10 mg/mL) of fucoidan (from Fucus vesiculosus) solution, and homogenized at 14,000 rpm for 1 minute using an IKA® DIGITAL ULTRA-TURRAX® T25 Homogenizer. The resulting emulsion was poured into 50 mL 0.1% Brij solution to harden the nanoparticles quickly and continued stirring magnetically at 400 rpm for 3-5 hours to ensure the evaporation of the solvent. The nanoparticles were purified three times with distilled water by tangential flow filtration (TFF). After three times of TFF wash the nanoparticles were found to have an average particle size of 638.8 nm and a zeta potential of −51.8 mV.

While this invention has been particularly shown and described with references to preferred embodiments thereof, it will be understood by those skilled in the art that various changes in form and details may be made therein without departing from the scope of the invention encompassed by the appended claims.

What is claimed is:

1. Particles having negative surface charges, comprising polylactide-co-glycolide (PLGA) and a sulfate polysaccharide, wherein the PLGA and the sulfate polysaccharide form an interpenetrating network.

2. The particles of claim 1, wherein the particles are microparticles or nanoparticles.

3. The particles of claim 1, wherein the particles have a zeta potential having an absolute value of at least about 25 mV.

4. The particles of claim 1, wherein the sulfate polysaccharide has a molecular weight between about 200 Da and 15 kDa.

5. The particles of claim 1, further comprising an active agent.

6. The particles of claim 5, wherein the active agent is encapsulated within the particle.

7. The particle of claim 1, wherein the sulfate polysaccharide is selected from the group consisting of heparan sulfate, carrageenan, fucoidan, and ulvan.

* * * * *